United States Patent
Khamar et al.

(10) Patent No.: US 9,789,187 B2
(45) Date of Patent: Oct. 17, 2017

(54) STABLE PHARMACEUTICAL COMPOSITION FOR ATHEROSCLEROSIS

(75) Inventors: Bakulesh Mafatlal Khamar, Ahmedabad (IN); Kumud Kumar Padhee, Ahmedabad (IN); Nilamkumari Somalal Patel, Ahmedabad (IN); Sunil Chowdary Koduri, Ahmedabad (IN); Amit Mukharya, Ahmedabad (IN); Indravadan Ambalal Modi, Ahmedabad (IN); Rajiv Indravadan Modi, Ahmedabad (IN)

(73) Assignee: Cadila Pharmaceuticals Limited, Ahmedabad (IN)

( * ) Notice: Subject to any disclaimer, the term of this patent is extended or adjusted under 35 U.S.C. 154(b) by 312 days.

(21) Appl. No.: 13/201,821

(22) PCT Filed: Feb. 8, 2010

(86) PCT No.: PCT/IB2010/000234
§ 371 (c)(1),
(2), (4) Date: Aug. 16, 2011

(87) PCT Pub. No.: WO2010/092450
PCT Pub. Date: Aug. 19, 2010

(65) Prior Publication Data
US 2012/0027849 A1 Feb. 2, 2012

(30) Foreign Application Priority Data

Feb. 11, 2009 (IN) ............................ 287/MUM/2009
Jul. 23, 2009 (IN) ......................... 1699/MUM/2009

(51) Int. Cl.
*A61K 45/06* (2006.01)
*A61K 31/445* (2006.01)
(Continued)

(52) U.S. Cl.
CPC ............. *A61K 45/06* (2013.01); *A61K 9/1623* (2013.01); *A61K 9/1652* (2013.01); *A61K 9/209* (2013.01);
(Continued)

(58) Field of Classification Search
CPC ........ A61K 45/06; A61K 31/00; A61K 9/209; A61K 9/2077; A61K 9/2886; A61K 9/4808; A61K 9/4866; A61K 9/5084
(Continued)

(56) References Cited

U.S. PATENT DOCUMENTS

2003/0068366 A1* 4/2003 Chungi et al. ................ 424/452
2003/0175344 A1 9/2003 Wald et al.
(Continued)

FOREIGN PATENT DOCUMENTS

GB 2482432 B 9/2013

OTHER PUBLICATIONS

Howard et al, "Does the Association of Risk Factors and Atheroscelerosis Change with Age?" American Heart Association, 1997, pp. 1-13.*
(Continued)

*Primary Examiner* — Rachael Bredefeld
(74) *Attorney, Agent, or Firm* — Pepper Hamilton LLP

(57) ABSTRACT

The present invention relates to a stable solid oral pharmaceutical multi-component composition comprising combination of blood pressure lowering drugs with lipid lowering agent/s and optionally a platelet aggregation inhibitor in a single dosage form. The blood pressure lowering agents are selected from β-adrenergic receptor blocking agent, ACE inhibitor and diuretic. The lipid lowering agent is selected from HMG Co-enzyme-A reductase inhibitor. The pharmaceutical composition made as per present invention a) overcomes any drug-drug interactions, b) exhibits pharmacoki- (Continued)

Mean Graph of Atenolol (N=30)

netic and pharmacodynamic profile of individual therapeutic agent, c) has minimal side effects. The invention provides multi-component composition (MCC) to increase adherences to therapy. The MCC as per present invention provides compositions that maintain activity of all active ingredients without significant increase in adverse event profile. The present invention further relates to a method of preparing the said pharmaceutical composition.

11 Claims, 5 Drawing Sheets

(51) Int. Cl.
  *A61K 31/00* (2006.01)
  *A61K 9/20* (2006.01)
  *A61K 9/16* (2006.01)
  *A61K 9/24* (2006.01)
  *A61K 9/28* (2006.01)
  *A61K 9/48* (2006.01)
  *A61K 9/50* (2006.01)

(52) U.S. Cl.
  CPC .......... *A61K 9/2054* (2013.01); *A61K 9/2077* (2013.01); *A61K 9/2846* (2013.01); *A61K 9/2866* (2013.01); *A61K 9/2886* (2013.01); *A61K 9/4808* (2013.01); *A61K 9/4866* (2013.01); *A61K 9/5084* (2013.01); *A61K 31/00* (2013.01); *A61K 31/445* (2013.01)

(58) Field of Classification Search
  USPC ........................................................ 424/451
  See application file for complete search history.

(56) References Cited

U.S. PATENT DOCUMENTS

2005/0026992 A1    2/2005  Sasmal et al.
2007/0116756 A1*   5/2007  Komireddi et al. .......... 424/451

OTHER PUBLICATIONS

International Search Report dated Jun. 15, 2010.
European Search Report (EPO Form 1703) dated Oct. 10, 2012 in European Patent Application No. 10 770 398.5 (Applicant: Dr. Reddy's Laboratories Ltd. et al.).
Communication dated May 3, 2013 in reply to the European Search Report in European Patent Application 10 770 398.5 (Applicant: Dr. Reddy's Laboratories Ltd. et al.).

* cited by examiner

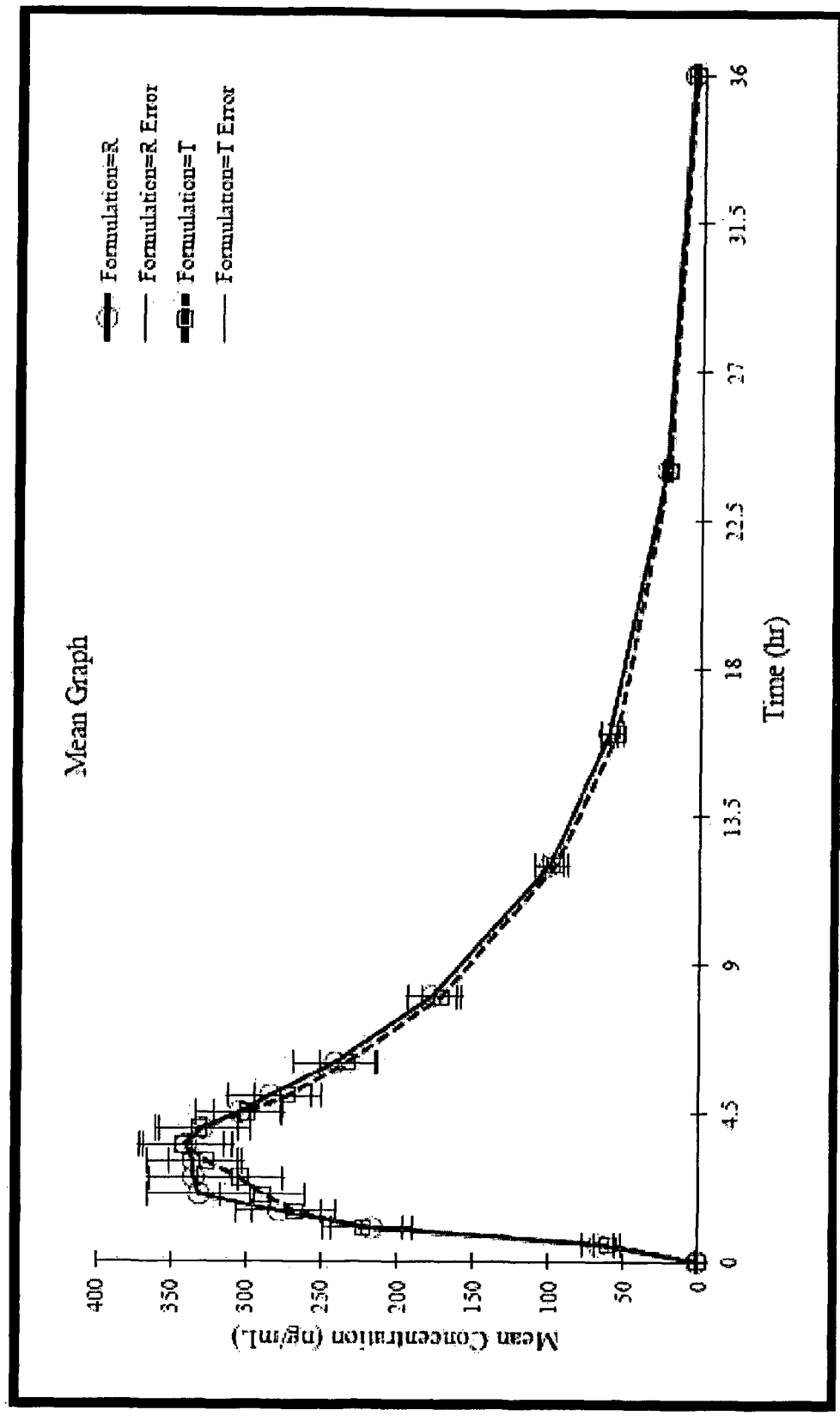
Figure 1: Mean Graph of Atenolol (N=30)

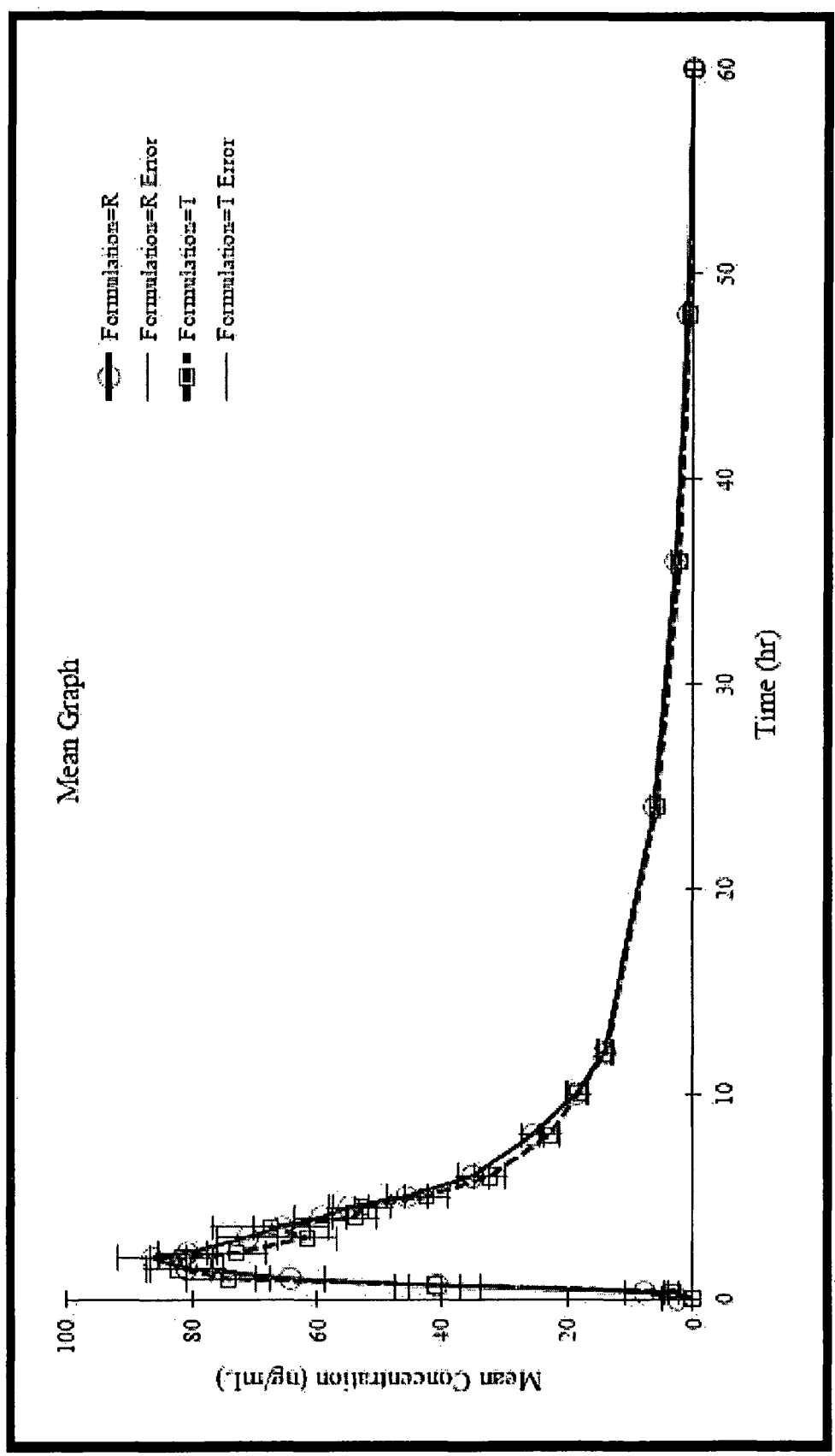
Figure 2: Mean Graph of Hydrochlorthiazide (N=32)

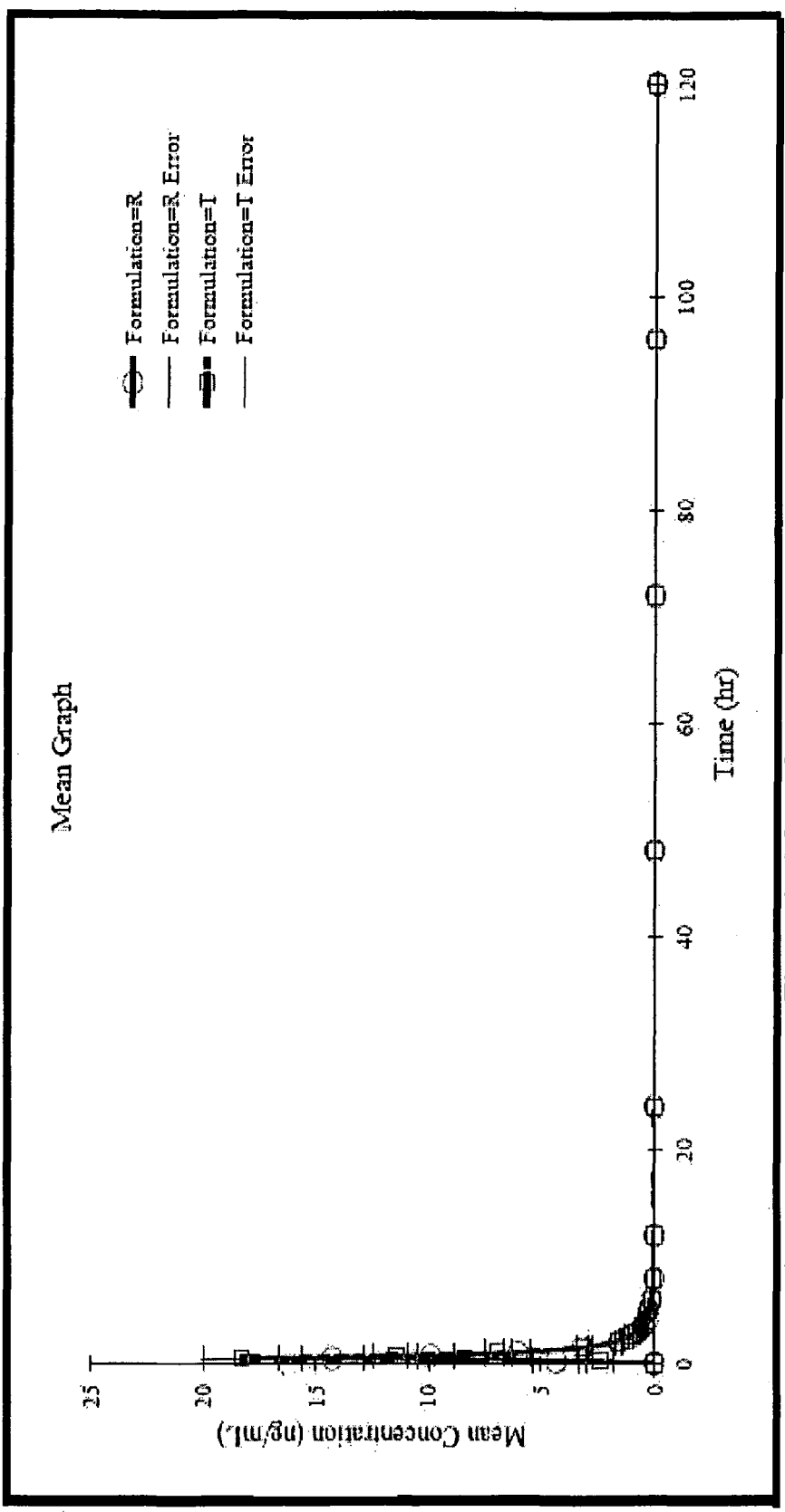
Figure 3 : Mean Graph of Ramipril (N=35)

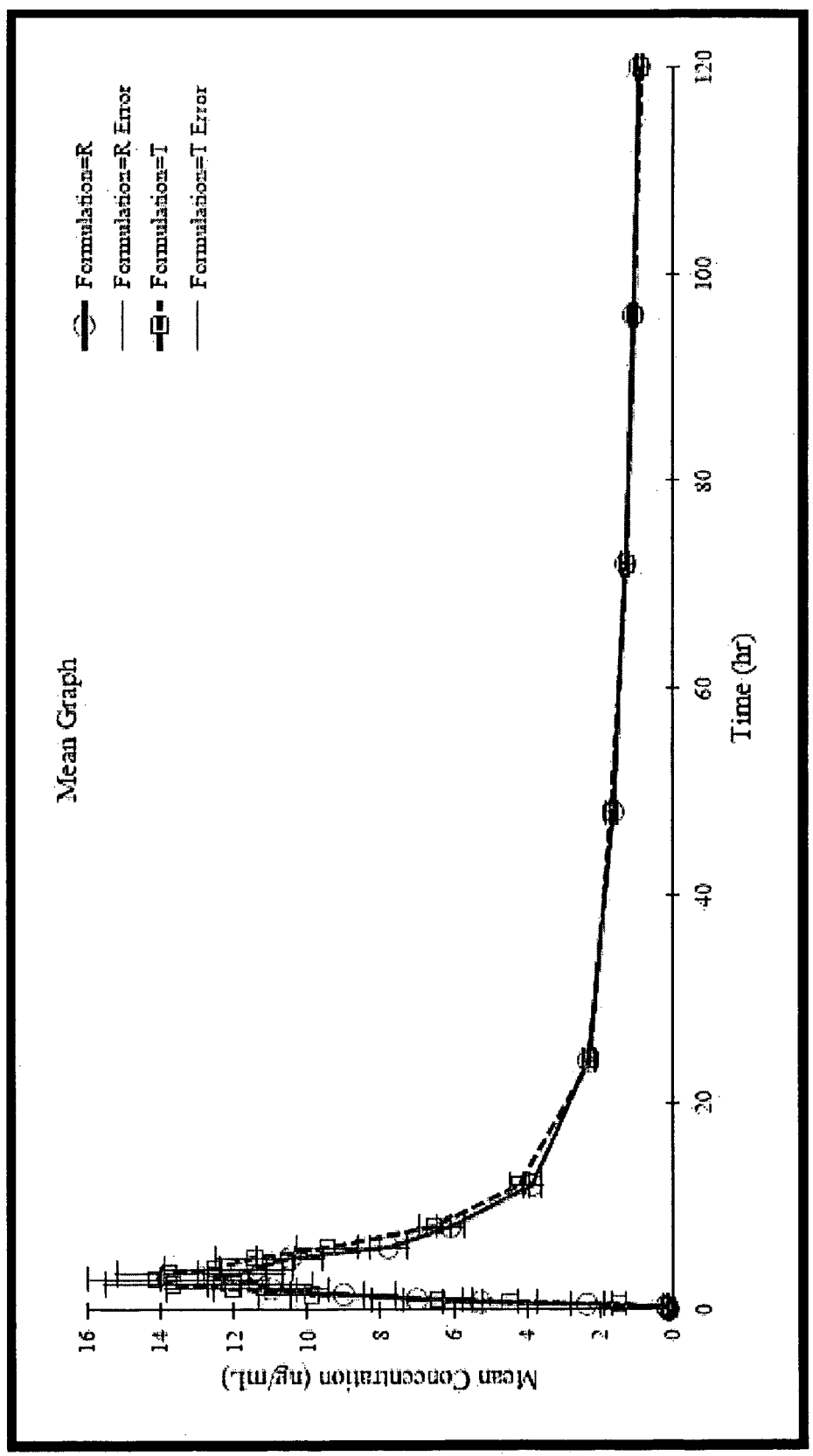
Figure 4 : Mean Graph of Ramiprilat (N=32)

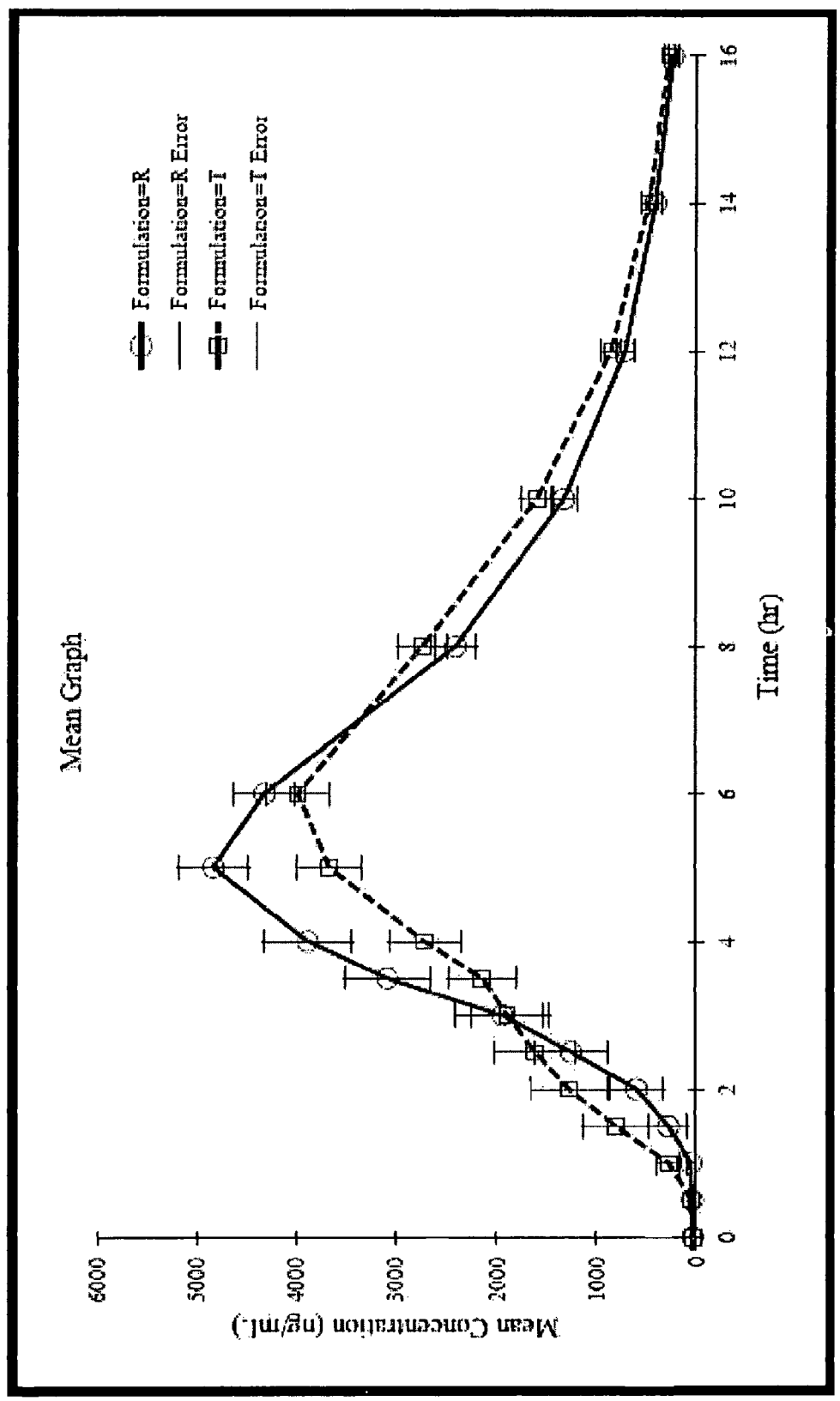
Figure 5: Mean Graph of Aspirin (N=32)

STABLE PHARMACEUTICAL COMPOSITION FOR ATHEROSCLEROSIS

FIELD OF THE INVENTION

This application is a national phase filing under 35 U.S.C. §371 of international patent application number PCT/IB2010/000234 filed Feb. 8, 2010 which claims priority to Indian patent applications number 1699/MUM/2009 filed Jul. 23, 2009 and 287/MUM/2009 filed Feb. 11, 2009, each of which is hereby incorporated by reference in its entirety.

The present invention relates to a stable solid oral pharmaceutical multi-component composition for management of atherosclerosis comprises of combination of blood pressure lowering drugs with lipid lowering agent/s and optionally a platelet aggregation inhibitor in a single dosage form, wherein the pharmaceutical composition a) overcomes any drug-drug interactions, b) exhibits pharmacokinetic and pharmacodynamic profile of individual therapeutic agent, c) has minimal side effects.

The invention provides multi-component composition (MCC) to increase adherences to therapy. The MCC as per present invention provides compositions that maintain activity of all active ingredients without significant increase in adverse event profile.

The present invention further relates to a method of preparing the said pharmaceutical composition.

BACKGROUND OF THE INVENTION

Atherosclerosis is a progressive disease characterized by the thickening, hardening and loss of elasticity of inner artery walls. It is the most common cause of morbidity and mortality in the western world, surpassing any other single degenerative disease. In the United States and most other developed countries, atherosclerosis is the leading cause of illness and death. Atherosclerosis caused almost 870,000 deaths in 2005—almost twice as many as cancer caused and 9 times as many as injuries caused.

The following conditions have been linked to atherosclerosis:
  Coronary artery disease
  Cerebrovascular disease
  Kidney disease leading to kidney failure and dialysis
  Peripheral vascular disease The fundamental pathology of vascular disease is an abnormal accumulation of cells within the subintimal space below the surface of the endothelial cell lining, resulting in a decrease in lumen size and tissue perfusion.

With narrowing, atherosclerosis usually does not produce symptoms until the interior of an artery is narrowed by more than 70%. The first symptom of a narrowed artery may be pain or cramps at times when blood flow cannot keep up with the tissues' need for oxygen. For instance, during exercise, a person may feel chest pain because the oxygen supply to the heart is inadequate. While walking, a person may feel leg cramps (intermittent claudication) because the oxygen supply to the leg muscles is inadequate. If the arteries supplying one or both kidneys become narrowed, kidney failure or dangerously high blood pressure can result. If the arteries supplying the heart (coronary arteries) are blocked, a heart attack can result. Blockage in the arteries supplying the brain can causes a stroke. Blockage of the arteries in the legs can cause gangrene of toe, foot, or leg. The risk factors for atherosclerosis include:

Smoking: The risk of atherosclerosis and related complications is 1.8 times higher in smokers. People who quit using tobacco have only half the risk of those who continue to use tobacco-regardless of how long they smoked before quitting. Quitting also decreases the risk of illness and death in people who have peripheral arterial disease. The benefits of quitting tobacco use begin immediately and increase with time.

Diabetes Mellitus: The risk of developing atherosclerosis is 2 to 6 times higher for people with diabetes, particularly women. These people also tend to develop atherosclerosis at an earlier age and more extensively than do people who do not have diabetes. Control of blood pressure in this group reduces the risk. Glycemic control is good for other complications of diabetes, has no effect on atherosclerosis.

Obesity: Obesity, Particularly abdominal (truncal) obesity, increases the risk of atherosclerosis.

Cholesterol levels: Total cholesterol and LDL cholesterol level are other important modifiable risk factors. Lowering high LDL cholesterol levels through the use of drugs like statins can significantly reduce the risk of morbidity and mortality related to atherosclerosis. The risk is decreased when the LDL cholesterol level is below 130 mg/dl (3.4 mmol/L). In high-risk people, such as those who have diabetes or who already have severe atherosclerotic disease like heart attacks, stroke, or bypass surgery, LDL cholesterol should be below 70 mg/dL (1.8 mmol/L) The desired level of total cholesterol is 140 to 200 mg/dL (3.6 to 5.2 mmol/L).

Blood Pressure: Blood pressure is a risk factor for atherosclerosis related morbidity and mortality e.g. heart attack and stroke. The risk of atherosclerotic cardiovascular disease starts increasing when blood pressure levels are above 110/75 mmHg. Reducing high blood pressure clearly lowers risk. This is in spite of the fact that blood pressure above 140/90 mm of Hg is considered high. The lowering of blood pressure reduces the risk of atherosclerosis related problems in hypertensives as well as non-hypertensives in a similar way. The prophylactic effect is proportional to no. of drugs (one vs two in Progress trial) used to manage B.P.

Anti-platelet agents: People who are at high risk for atherosclerosis also may benefit from taking aspirin or other anti platelet drugs. Aspirin benefit is identical with low as well as high dosage.

Atherosclerosis management in general involves multiple drugs like lipid lowering, blood pressure lowering (more than one), platelet aggregation inhibitors and needs to be taken for regular extended of periods. However there are problems associated with multiple medicines when taken for a long durations.

a) adherence: Unfortunately, adherence may fall as number of drug increases. Swallowing of multiple tablets is likely to lead in non adherence to dosing schedule. It is reported that about 25% medicines when prescribed for long-term conditions, are not taken as directed. Increased numbers of medicines also increase nonadherence.

Reducing pill burden improves adherens (*Arch Intern Med.* 2005; 165:1147-1152). Improvements in adherence have been seen in a single pill combination of atorvastatin and amlodipine versus a two-pill combination. In a retrospective analysis of pharmacy claims data, this single pill strategy was associated with a two- to threefold improvement in likelihood of adherence.

b) Compliance: Compliance also becomes an issue with multiple medication usage. The multi-component pharmaceutical composition (MCPC) is useful in improving compliance and adherence to therapy.

Despite the need for multi-component pharmaceutical compositions, they have not been commercialized yet due to their inherent problems associated with such compositions especially with regard with stability, drug-drug interaction leading to changes in pharmacokinetic and pharmacodynamic properties.

Even two drug combinations are met with difficulties.

Some of the known examples of alterations changes in pharmacokinetic and pharmacodynamic parameters seen between two drugs belong to a group of antihypertensives, lipid lowering drugs and or antiplatelet agents.

a. Amlodepine (antihypertensive drug) increases AUC of simvastatin (lipid lowering drug) by 30%.
b. Diltiazem (antihypertensive drug) increases AUC of simvastatin (lipid lowering drug) by two fold.
c. Nisoldipine (antihypertensive drug) increases AUC of telmisartan (antihypertesive drug) by 132%.
d. Verapamil and diltiazem (antihypertensive drugs) are known to increase serum level of atorvastatin, simvastatin, lovastatin, fluvastatin but not of pravastatin and rosuvastatin (Statins).
e. Aspirin (Antiplatelet agent) decreases antihypertensive effect of ACE inhibitors.
f. Aspirin (Antiplatelet agent) decreases effects of diuretics.
g. Aspirin (Antiplatelet agent) may decrease pharmacological effects of spironolactone (diuretics).
h. Aspirin (Antiplatelet agent) decreases hypotensive effects of betablockers.
i. Verapamil (antihypertensive agent) when used with betablockers (antihypertensives) I is known to induce brady-cardia and heart failure.
j. Diltiazem (antihypertensive agent) when used with proparanolol (antihypertensives) is known to induce brady-cardia and heart failure.
k. ACE inhibitor (antihypertensive) when used with beta-blockers (antihypertensive) induces hypotension.
l. Propanolol (antihypertensive) when used with ACE inhibitor (antihypertensive agents), results into increased hyper-reactivity.
m. Use of ramipril (ACE inhibitor, antihypertensive) and diuretic are known to induce excessive reduction in blood pressure (hypotension) on initiation of therapy.
n. Amlodepine is known to reduce antiplatelet activity of clopidogrel Drug-drug interaction also takes place in a formulation due to physical and chemical incompatibility. The physical mixture on intimate mixing resulted in incompatibility. Following are some of the examples:
1) Simvastatin+Ramipril+Aspirin
2) Simvastatin+Ramipril+Hydrochlorothiazide
3) Aspirin+Ramipril+Hydrochlorothiazide
4) Simvastatin, Ramipril, Hydrochlorothiazide and Atenolol
5) Atenolol and Simvastatin European Patent No. 1611886 A1 relates to a combination of an inhibitor of the renin angiotensin system, optionally an additional antihypertensive agent, a cholesterol lowering agent, a diuretic, and aspirin, which can be administered to prevent cardiovascular disorders. The patent does not address issues relates to about the stability related issues, drug-drug interaction, suitable dosage form having patient compliance. The patent mainly discloses about effects of Ramipril, an inhibitor of the renin angiotensin system in prevention or reduction of a cardiovascular event in a high risk patient with no evidence of left ventricular dysfunction or heart failure, where the cardiovascular event is stroke, cardiovascular death or myocardial infarction. Based on current prosecution status, this patent application is withdrawn in European patent office. The present application is deemed to be withdrawn on 30 Oct. 2009 as per EP register.

European Patent No. 1272220 B1 discloses a pharmaceutical formulation that contains at least two agents that lower blood pressure, having different modes of action, plus an active agent from at least two of: lipid regulating agents; platelet function altering agents; and serum homocysteine lowering agents. It is preferred in this patent application to provide at least some of the drugs in smaller amounts than their customary therapeutic doses. The patent is silent about the stability related issues, drug-drug interaction, method of preparing the composition, pharmacokinetic and pharmacodynamic results. Based on current prosecution status, this patent application is under appeal in European patent office.

An article by N. J. Wald et al. "A Strategy to Reduce Cardiovascular Disease by More Than 80%," British Medical Journal, Vol. 326, pp. 1419-1423, 2003, advocates the daily prophylactic treatment of everyone over age 55, and everyone with existing cardiovascular disease, with a "Polypill" containing the following six drugs: a drug to lower cholesterol, such as either atorvastatin (10 mg) or simvastatin (40 mg), the combination of three blood pressure lowering drugs from different classes, such as a thiazide; a, Beta-blocker, and an ACE inhibitor, folic acid (0.8 mg), and aspirin (75 mg). The article doesn't discloses the formulation related details, drug-drug interaction, method of preparing the composition, stability related issues.

U.S. Patent application 20050026992 discloses pharmaceutical dosage form for treating or preventing cardiovascular events comprises therapeutic amounts of: a beta-adrenergic receptor antagonist, a diuretic, or both; a cholesterol-lowering agent; an inhibitor of the renin-angiotensin system; and aspirin. This application doesn't discuss about stability of the pharmaceutical dosage form. The patent application is also silent over bioequivalence information. The present prosecution status as per USPTO appears that the patent application has been given final rejection from USPTO examiner.

PCT application WO/2007/098390 A2 discloses new use of darusentan for adjunctive administration with a baseline antihypertensive regimen that comprises administration of at least one diuretic and at least two antihypertensive drugs selected from at least two of (a) ACE inhibitors and angiotensin II receptor blockers, (b) beta-adrenergic receptor blockers and (c) calcium channel blockers, to lower blood pressure in a patient having resistant hypertension. The patent application is mainly related to new use of darusentan. The patent is silent about the stability related issues, drug-drug interaction, suitable dosage form having patient compliance in terms of formulation weight, ease of administration and the like.

U.S. Patent application 20070116756 discloses pharmaceutical dosage form for treating or preventing cardiovascular events comprises therapeutic amounts of: a beta-adrenergic receptor antagonist, a diuretic, or both; a cholesterol-lowering agent; an inhibitor of the renin-angiotensin system; and aspirin. The patent application discloses maximum of four active agents in the formulation. The stability data of Example 1 doesn't disclose the stability of all active agents used in the formulation.

The presence of multiple drugs in a single formulation can lead to various issues including drug-drug interaction. This interaction is evident in following literature.

An article by Shinichiro Nishio et al. "Interaction Between Amlodipine And Simvastatin In Patients With Hypercholesterolemia And Hypertension" *Hyprtens*

*Res* Vol. 28 No. 3 (2005) pg 223-227 discloses that calcium channel blocker, amlodipine affects the plasma concentration of HMG-CoA reductase inhibitor, simvastatin.

An article by Henry L. Elliott et al. "The Interactions Between Nisoldipine And Two β Adrenoceptor Antagonists—Atenolol And Propranolol" *Br. J. Clin. Pharmac.* (1991), 32, pg 379-385 discloses that steady state plasma concentrations of both β-adrenoceptor antagonists were significantly altered by the addition of nisoldipine.

An article by Mansoor Rastegarpanah et al. "A New Horizon In Primary Prevention Of Cardiovascular Disease, Can We Prevent Heart Attack By "Heart Polypill"" discloses Polypill has been the subject of great deal of debate. There is no evidence from randomized controlled trials that the treatment would be effective. There are still issues regarding its design, synthesis, pharmacokinetics, pharmacodynamics, bioequivalence, interactions, and evidence of clinical efficacy, adverse effects and safety.

An article by Ivancica et al. "Interaction between Antihypertensives and NSAIDS in primary care: a controlled trial" discloses that NSAIDS like Piroxicam and Ibuprofen markedly blunt the effect of antihypertensive drugs.

Thus, the presence of many drugs or active agents in a single solid oral composition can lead to various problems related to physical, chemical stability of the dosage form and the drugs. These drugs may react with each other (drug-drug interaction) or the excipients present in the composition and ultimately lead to unstable formulation. Further there are chances that one drug will alter the bioavailability of the other drug.

It is very difficult to adjust the absorption of different active agents from single solid oral composition. Usually in practice, the absorption of one of the active agents may decrease while that of the other one increases. When selecting the pharmaceutical excipients, to be used in a pharmaceutical composition in combination with several active agents, numerous factors have to be considered, e.g., the chemical and physical characteristics of the active agents and excipients, the bioavailabilities of the active agents, the method of preparing the composition, the stability of the composition and the like.

As disclosed in various prior art that combination of multiple active drugs in single formulation leads to drug-drug interaction. Such drug-drug interaction may result in following possibilities in combination of active drugs based on Multi-constituent cardiovascular pill (MCCP) or multi-component pharmaceutical composition (MCPC):

1. Loss of activity of any of active ingredient.
2. Increase in adverse event profile as compared to single active drug included in the composition.
3. Variability in serum level of antihypertensive drugs which is achieved by consumption of a single ingredient or active drug.
4. Reduction in sitting systolic and diastolic B.P. as compared to single ingredient or active drug.
5. Significant differences in heart rate, lipid levels, serum concentration, as compared to single ingredient or active drug.

Neither of the above-cited patents nor any other publication, of which applicants are aware, describes a solid oral composition which has resolved the above mentioned issues.

Further, in accordance with the recommendations made by the World Health Organization to develop combination products for cardiovascular therapy and test their efficacy in high risk individuals, it is highly desirable to develop combination products using a diverse cardiovascular drug/s including adrenergic blocking agent, a diuretic, a cholesterol-lowering agent, an inhibitor of the renin-angiotensin system, and aspirin.

It is a long-standing need in the pharmaceutical industry to provide stable pharmaceutical composition comprising combination of adrenergic receptor blocking agent, HMG Coenzyme-A reductase inhibitor, renin-angiotensin enzyme inhibitor, diuretic and platelet aggregation inhibitor in a single dosage form with less side effects and more efficacy and better patient compliance as compared to individual active ingredient.

DESCRIPTION OF DRAWINGS

FIG. 1: The graph showing Atenolol with no gain or loss in bioavailability and drug-drug interaction.

FIG. 2: The graph showing Hydrochlorothiazide with no gain or loss in bioavailability and drug-drug interaction.

FIG. 3: The graph showing Ramipril with no gain or loss in bioavailability and drug-drug interaction.

FIG. 4: The graph showing Ramiprilat with gain or loss in bioavailability and drug-drug interaction.

FIG. 5: The graph showing Aspirin with no gain or loss in bioavailability and drug-drug interaction.

SUMMARY OF THE INVENTION

The main object of the invention is to provide a stable solid oral pharmaceutical composition for management of atherosclerosis comprises of combination of adrenergic receptor blocking agent, HMG Coenzyme-A reductase inhibitor, renin-angiotensin enzyme inhibitor, diuretic and platelet aggregation inhibitor wherein the pharmaceutical composition is a) devoid of drug-drug interaction, b) having identical pharmacokinetic and pharmacodynamic profile of individual therapeutic agent, c) with minimal side effects.

Another object of the invention is to provide a stable pharmaceutical composition for management of atherosclerosis, wherein the said pharmaceutical composition comprises of combination of adrenergic receptor blocking agent, HMG Coenzyme-A reductase inhibitor, renin-angiotensin enzyme inhibitor, diuretic and platelet aggregation inhibitor.

Another object of the invention is to provide a stable pharmaceutical multi-component composition and a process for manufacturing a composition for management of atherosclerosis comprising of combination of adrenergic receptor blocking agent, HMG Coenzyme-A reductase inhibitor, renin-angiotensin enzyme inhibitor, diuretic and/or platelet aggregation inhibitor or their pharmaceutically acceptable salts, solvates, enantiomers or mixtures thereof in a single dosage form.

Another object of the present invention is to provide a stable solid oral pharmaceutical composition comprising adrenergic receptor blocking agent, HMG Coenzyme-A reductase inhibitor, renin-angiotensin enzyme inhibitor, diuretic and platelet aggregation inhibitor wherein at least one active ingredient is separated from other active ingredients.

Another object of the present invention is to provide a stable solid oral pharmaceutical composition comprising adrenergic receptor blocking agent, HMG Coenzyme-A reductase inhibitor, renin-angiotensin enzyme inhibitor, diuretic and platelet aggregation inhibitor wherein at least two active ingredients are separated from other active ingredients.

Another object of the present invention is to provide a stable solid oral pharmaceutical composition comprising adrenergic receptor blocking agent, HMG Coenzyme-A reductase inhibitor, renin-angiotensin enzyme inhibitor, diuretic and platelet aggregation inhibitor wherein at least three active ingredients are separated from other active ingredients.

Another object of the present invention is to provide a stable solid oral pharmaceutical composition comprising combination of HMG Coenzyme-A reductase inhibitor, adrenergic receptor blocking agent renin-angiotensin enzyme inhibitor, diuretic, platelet aggregation inhibitor and at least one pharmaceutically acceptable excipient, wherein the therapeutic effect achieved with the composition in the management of atherosclerosis is comparable to that achieved with the known separate formulations of HMG Coenzyme-A reductase inhibitor, adrenergic receptor blocking agent renin-angiotensin enzyme inhibitor, diuretic, platelet aggregation inhibitor, which are administered concomitantly, at the same doses of the active agents as the combination formulation of the invention.

Another object of the present invention is to provide a stable solid oral pharmaceutical composition comprising combination of HMG Coenzyme-A reductase inhibitor, adrenergic receptor blocking agent renin-angiotensin enzyme inhibitor, diuretic, platelet aggregation inhibitor and at least one pharmaceutically acceptable excipient, wherein the composition is pharmacokinetically comparable to the known formulations of HMG Coenzyme-A reductase inhibitor, adrenergic receptor blocking agent, renin-angiotensin enzyme inhibitor, diuretic, platelet aggregation inhibitor formulations used herein as a reference, administered concomitantly at the same doses of active agents as the composition of the invention.

Another object of the present invention is to provide a stable solid oral pharmaceutical composition comprising combination of HMG Coenzyme-A reductase inhibitor, adrenergic receptor blocking agent renin-angiotensin enzyme inhibitor, diuretic, platelet aggregation inhibitor and at least one pharmaceutically acceptable excipient, wherein the composition is substantially bioequivalent with the known formulations, e.g. the bioavailability achieved with the composition of the invention is at levels comparable to that achieved with the concomitant administration of the same doses of the known separate formulations of HMG Coenzyme-A reductase inhibitor, adrenergic receptor blocking agent, renin-angiotensin enzyme inhibitor, diuretic, platelet aggregation inhibitor formulations used herein as a reference.

Another object of the invention is to provide a stable pharmaceutical composition for management of atherosclerosis, wherein the said pharmaceutical composition comprises combination of adrenergic receptor blocking agent, HMG Coenzyme-A reductase inhibitor, renin-angiotensin enzyme inhibitor, diuretic and platelet aggregation inhibitor in a single dosage form wherein the composition provides improved patient compliance, adherence to the medication.

Another object of the invention is to provide a pharmaceutical composition for management of atherosclerosis, wherein the said pharmaceutical composition comprises combination of adrenergic receptor blocking agent, HMG Coenzyme-A reductase inhibitor, renin-angiotensin enzyme inhibitor, diuretic and platelet aggregation inhibitor wherein the composition has minimal side effects and without drug-drug interaction.

Yet another object of present invention is to provide a pharmaceutical composition for management of Atherosclerosis where in multiple ingredients are formulated in such a way that there is no loss of activity of any of active ingredient.

Yet another object of invention is to provide a pharmaceutical composition for management of atherosclerosis where in multiple ingredients are formulated in such a way that adverse event profile is not worse than a single ingredient included in the composition.

Yet another object of invention is to provide a pharmaceutical composition for management of atherosclerosis comprising of more than one antihypertensive drug which when consumed provides serum level of antihypertensive drugs which are no different then achieved by consumption of a single ingredient.

Yet another object of present invention is to provide a pharmaceutical composition for management of atherosclerosis comprising of anti-platelet agent along with other ingredients in such a way that its consumption do not result in blood levels identical to achieved with consumption of anti-platelet agent alone.

Yet another object of present invention is to provide a pharmaceutical composition for management of atherosclerosis comprising of antihypertensive drugs and a lipid lowering drugs in such a way that its consumption does not result in blood levels to active metabolite lower than the one achieved with consumption of a lipid lowering agent alone.

Yet another object of present invention is to provide a pharmaceutical composition comprising of multiple antihypertensive drugs in such a way that effect on sitting systolic and diastolic B.P. is more than each ingredient.

Yet another object of present invention is to provide a pharmaceutical composition comprising of multiple antihypertensive drugs (three or more) in such a way that effect on sitting systolic and diastolic B.P. is more than what is seen with two of three or three of four antihypertensive drugs.

Yet another object of present invention is to provide a pharmaceutical composition containing β-blocker as one of active ingredient where in reduction in heart rate is non inferior to those seen with other atenolol containing compositions.

Yet another object of present invention is to provide a pharmaceutical composition containing lipid modifying drugs in such a way that effect on lipid is non inferior to that observed when lipid modifying drug is taken alone.

Yet another object of present invention is to provide a method of management of atherosclerosis comprising administration of a pharmaceutical composition comprising multiple ingredient where in ingredients are selected and formulated in such a way that serum level of antihypertensive drugs are not inferior to those achieved with administration of a pharmaceutical composition containing a single identical antihypertensive drug.

Yet another object of present invention is to provide a method of management of atherosclerosis comprising administration of a pharmaceutical composition which has multiple ingredients as an active components which are selected and formulated in such a way that serum level of lipid lowering active metabolite is not inferior to that which is achieved when lipid lowering drug is administered alone.

Yet another object of present invention is to provide a method of management of atherosclerosis by a pharmaceutical composition comprising of multiple ingredients, one of which is antiplatelet agent, consumption of which results in serum level of antiplatelet agent which not inferior to the serum levels achieved when antiplatelet agent is consumed alone.

Yet another object of present invention is to provide a method of management of atherosclerosis which comprises of administration of multiple ingredients in a single pharmaceutical composition which is formulated in such a way that none of the active ingredients achieve serum levels of actives on consumption which is inferior to the serum levels obtained following administration of any one of the active in isolation.

Yet another object of present invention is to provide a method of management of atherosclerosis comprises of administration of pharmaceutical composition containing multiple ingredient whose blood pressure lowering effect is non inferior to that obtained with all blood pressure lowering drug in combination with each other or in isolation.

Yet another object of present invention is to provide a method of management of atherosclerosis by administration of a B-blocker as one of the multi-component of a pharmaceutical composition resulting in reduction in heart rate which is non-inferior to the one achieved with B-blocker containing pharmaceutical composition.

Yet another object of present invention is to provide a method of management of atherosclerosis comprises of administration of lipid lowering agent along with other multiple agent in a single pharmaceutical composition formulated in such a way that effect of lipid lowering agent is non inferior to lipid modifying results obtained when lipid lowering drug is administered alone.

Yet another object of present invention is to provide a method of management of atherosclerosis by administration of antiplatelet agent along with other active ingredients in a single pharmaceutical composition formulated in such a way that effect of their ingredient is non inferior to those seem when other ingredients are administered alone or a group in absence of antiplatelet agent.

Yet another object of present invention is to provide a method of management of atherosclerosis by administration of antiplatelet agent and lipid modifying agent along with other active ingredients in a single pharmaceutical composition which is formulated in such a way that effect of other ingredients is not inferior to those obtained with administration of pharmaceutical composition not containing antiplatelet, agents and lipid modifying agents.

Yet another object of present invention is to provide a method of management of atherosclerosis by administration of multi-component pharmaceutical composition formulated in such a way that adverse event profile is comparable to its components.

Yet another object of present invention is to provide a method of management of atherosclerosis by administration of multi-component pharmaceutical composition formulated in such a way that antihypertensive effect is superior to its components containing lower number of antihypertensive drugs.

DETAILED DESCRIPTION OF THE INVENTION

Before the present methods and compositions are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

The singular forms "a", "an", and "the" as used in this specification and the appended claims include plural references unless the context clearly dictates otherwise. Thus for example, a reference to "a method" includes one or more methods, and/or steps of the type described herein and/or which will become apparent to those persons skilled in the art upon reading this disclosure and so forth.

The term "Multi-constituent cardiovascular pill" (MCCP) or "multi-component pharmaceutical composition" (MCPC) or "Multi Component Composition" (MCC) as used herein means solid oral dosage form comprising combination of, HMG Coenzyme-A reductase inhibitor, adrenergic receptor blocking agent renin-angiotensin enzyme inhibitor, diuretic and/or optionally platelet aggregation inhibitor.

The term "minimal side effects" as used herein means that the side effects of solid oral pharmaceutical composition comprises combination of HMG Coenzyme-A reductase inhibitor, adrenergic receptor blocking agent, renin-angiotensin enzyme inhibitor, diuretic, platelet aggregation inhibitor is less than side effects of a single active ingredient included in the composition.

The term "devoid of drug-drug interaction" or "without drug-drug interaction" as used herein means that the individual active ingredient in solid oral pharmaceutical composition comprises combination of HMG Coenzyme-A reductase inhibitor, adrenergic receptor blocking agent, renin-angiotensin enzyme inhibitor, diuretic, platelet aggregation inhibitor doesn't alter the physical stability or chemical stability or pharmacokinetic property or pharmacodynamic property of other active ingredient.

The term "no loss of activity" as used herein means that the pharmacological activity of any individual active ingredient in solid oral pharmaceutical composition is inferior to pharmaceutical composition comprising combination of HMG Coenzyme-A reductase inhibitor, adrenergic receptor blocking agent renin-angiotensin enzyme inhibitor, diuretic, platelet aggregation inhibitor.

The term "drug" or "active ingredient" or "active agent" as used herein is related to HMG Coenzyme-A reductase inhibitor or adrenergic receptor blocking agent or renin-angiotensin enzyme inhibitor or diuretic or platelet aggregation inhibitor or combination thereof.

The term "inactive" or "pharmaceutically acceptable excipient" or "excipient" or "ingredients" as used herein is related to commonly known pharmaceutically inactive compounds which can be used for the preparation of stable pharmaceutical composition thereof. The pharmaceutically inactive compounds used in present invention preferably don't include organic acid(s).

The term "stable pharmaceutical composition" for the purpose of this invention is defined as a pharmaceutical composition without significant drug-drug interaction between the active ingredients and exhibiting no significant changes in colour, physical characteristics and potency of active ingredients (potency loss not more than 10% of label claim). The stable pharmaceutical composition as per present invention is also bioequivalent. (T/R ratio of geometric means within 80-125%).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications Mentioned herein are incorporated herein by reference to describe the methods and/or materials in connection with which the publications are cited.

The present invention relates to a pharmaceutical composition for management of atherosclerosis, wherein the said pharmaceutical composition comprises of combination of, HMG Coenzyme-A reductase inhibitor, adrenergic receptor blocking agent renin-angiotensin enzyme inhibitor, diuretic and platelet aggregation inhibitor which constitutes Multi-constituent cardiovascular pill (MCCP) or multi-component pharmaceutical composition (MCPC).

HMG coenzyme A reductase catalyzes the conversion of HMG-COA to mevalonate, which is a rate-limiting step in the biosynthesis of cholesterol. Inhibitors of HMG Co-A reductase are useful as cholesterol or lipid lowering agents. Useful cholesterol-lowering agents include but are not limited to HMG CoA reductase inhibitors, bile acid sequestrants, probucol, fibric acid agents and intestinal cholesterol absorption inhibitors like ezetimibe. HMG-COA reductase inhibitors are among the useful cholesterol reducing agents for the present invention. HMG-COA reductase inhibitors or lipid modifying agents that may be used in the present invention include, but are not limited to atorvastatin, pravastatin, cerivistatin, fluindostatin, fluvastatin, lovastatin, mevastatin, rosuvastatin, pitvastatin, dalvastatin and velostatin. The preferred HMG Co-A reductase inhibitor used in the instant invention is simvastatin. Preferably, Simvastatin is present in the dosage form in an amount ranging from 2 mg to 80 mg.

Adrenergic receptor blocking agent competitively inhibits binding of norepinephrine to its receptors, and used in the treatment of essential hypertension. These drugs include atenolol, bisoprolol, labetolol, metoprolol, propranolol, nebivolol and the like. The preferred adrenergic receptor blocking agent used in the instant invention is β-adrenergic receptor blocking agent such as Atenolol. Preferably, Atenolol is present in the dosage form in an amount ranging from 2 mg to 100 mg.

Inhibition of the renin-angiotensin system by the angiotensin converting enzyme ("ACE") results in decreased plasma levels of angiotensin II, which leads to decreased vasopressor activity and aldosterone secretion. Inhibitors of the renin-angiotensin system are classified as ACE inhibitors. ACE inhibitors that are useful in the present invention include, but are not limited to, captopril, cilazapril, delapril, enalapril, fentiapril, fosinopril, indolapril, lisinopril, perindopril, pivopril, quinapril, ramipril, spirapril, trandolapril, and zofenopril. The preferred ACE inhibitor used in the instant invention is Ramipril. Preferably, Ramipril is present in the dosage form in an amount ranging from 0.5 mg to 20 mg.

Diuretics that are useful in the present invention include, but are not limited to, the drugs bendroflumethazide, chlorthiazide, chlorthalidone, hydrochlorthiazide, hydroflumethazide, indapamide, methyclothazide, metolazone, mefruside, polythiazide, trichlormethazide, cyclopenthiazide, polythiazide, qiunethazone and xipamide. The preferred diuretic used in the instant invention is Hydrochlorthiazide. Preferably, Hydrochlorothiazide is present in the dosage form in an amount ranging from 5 mg to 50 mg.

Platelet aggregation inhibitor affect platelet function by primarily inhibiting platelet cyclooxygenase ("COX") thereby prevents the formation of the aggregating agent thromboxane A2. This action is irreversible and the effects last for the lifetime of the platelet. Anti-platelet aggregating agents like aspirin, dipyridamole, and clopidogrel are useful in the present invention. Aspirin chemically is acetylsalicylic acid. The preferred Platelet aggregation inhibitor used in the instant invention is Aspirin. Preferably, aspirin is present in the dosage form in an amount ranging from 50 mg to 200 mg.

The low dose drug combination products could provide equal or enhanced efficacy with potentially reduced adverse effects.

The problems are associated with the fixed dose combinations. In fixed dose combinations, when we have found that enteric coated aspirin tablets are manufactured according to prior art were removed from the pan as in commercial production, the shock of the falling of the tablets from two to three feet and the impinging of the falling tablets upon the tablets already in the holding bin, creates micro fissures in the enteric coating which could not be seen under a microscope but which nevertheless causes the enteric coated tablets to fail the U.S.P. enteric test.

It was surprisingly found that the use of moisture coating of cellulose polymer preferably Hydroxypropyl methylcellulose absorbs the shocks during commercial production and protects the enteric coating of Aspirin tablet and also provides the better stability. Further, the overcoating after enteric coating provides the protection against moisture to the tablet and hence improves the stability.

Simvastatin tablet are available in market with a brand name Zocor®. Zocor® are film-coated tablets, consist of core tablets surrounded by a water-soluble film coating. The labeling for Zocor® tablets indicate that the excipients (i. e. inactive ingredients) used in the core tablets are lactose, cellulose, starch, magnesium stearate, ascorbic acid, citric acid and butylated hydroxyanisole.

Simvastatin is prone to degradation due to oxidation of the diene and oxidation of the hydroxyl group in the simvastatin molecule. The innovator product includes ascorbic acid and citric acid as excipients in the core tablets. Ascorbic acid is apparently included in the tablets as antioxidants. Citric acid is apparently added because it has chelation properties with metal ions, which, in the absence of the citric acid, could catalyze the oxidation process. The composition of the Zocor® core tablets is thus relatively complex in terms of the number of excipients used.

We have surprisingly found that the simvastatin tablet can also provide a better stability by eliminating the essential excipients of Zocor® tablet like ascorbic acid and citric acid. Thus applicant's formulation is more economical with less excipients and manufacturing process step.

Ramipril tablet are available in market with a brand name Altace®. Ramipril rapidly undergoes decomposition leading to diketopiperazine as decomposed product. Applicants have surprisingly found that when Ramipril was coated with various polymers which provide better flowability and enhanced stability as compared to non-polymer based Ramipril compositions.

Atenolol tablets are available in market with a brand name Tenormin®. The labeling for Tenormin® tablets indicate that the excipients (i. e. inactive ingredients) used in the tablets are Magnesium stearate, microcrystalline cellulose, povidone, sodium starch glycolate. Applicant provides the formulation in an economical way with less excipients and manufacturing process steps We have found that, mere admixture of active ingredients like Simvastatin, Ramipril, Atenolol and Hydrochlorothiazide blend with Aspirin tablet does not provide a stable pharmaceutical composition. The pharmaceutical composition prepared by mere admixing the active ingredients is incompatible with pharmaceutical excipients. The pharmaceutical composition optionally without using Aspirin is also not stable when prepared by mere admixing the other active ingredients. Thus the reformulation of each active ingredient is required in such a way that when all active ingredients kept in a single dosage form, the pharmaceutical composition should remain stable.

Thus there is a need to devise a new composition which remains stable during manufacturing and through out the shelf life when stored at recommended condition of temperature and humidity in a suitable pack configuration.

In one of the embodiment to provide a stable solid oral pharmaceutical composition comprising adrenergic receptor blocking agent, HMG Coenzyme-A reductase inhibitor, renin-angiotensin enzyme inhibitor, diuretic and platelet aggregation inhibitor wherein at least one active ingredient is separated from other active ingredients.

The separation of at least one active ingredient with other active ingredients in a single dosage form can be physical separation like the active ingredient which needs to be separated can be in the form of tablets, pellets, granules by granulation and/or coating process wherein the direct physical contact of other active ingredient is minimized or removed.

The MCPC composition is formulated as per given non-limiting examples in any combination as described below which provides a stable pharmaceutical dosage form.
1. 3 Tablets+Blend [Aspirin Tablet+Atenolol Tablet+Simvastatin Tablet+(Ramipril+HCTZ blend)]
2. 2 Tablets+Blend
   a. [Aspirin Tablet+Simvastatin Tablet+(Atenolol+Ramipril+HCTZ blend)]
   b. [Aspirin Tablet+Atenolol Tablet+(Simvastatin+Ramipril+HCTZ blend)]
3. 1 Tablet+Blend [Aspirin Tablet+(Atenolol+Simvastatin+Ramipril+HCTZ blend)]
4. All blend [Aspirin granules+Atenolol+Simvastatin+Ramipril+HCTZ blend]
5. 2 Tablets+Blend [Atenolol Tablet+Simvastatin Tablet+(Ramipril+HCTZ blend)]
6. 1 Tablet+Blend
   a. [Atenolol Tablet+(Simvastatin+Ramipril+HCTZ blend)]
   b. [Simvastatin Tablet+(Atenolol+Ramipril+HCTZ blend)]
   c. [Atenolol Tablet+Ramipril coating (Simvastatin+HCTZ blend)]
7. All blend [Atenolol+Simvastatin+Ramipril+HCTZ blend]

For all the active agents, the dosage is selected to prevent atherosclerosis whilst minimizing the undesirable side effects.

The diluents used as per present invention to provide a solid oral pharmaceutical composition include but not limited to microcrystalline cellulose, silicified microcrystalline cellulose, lactose, starch, pregelatinized starch, sugar, mannitol, sorbitol, dextrates, dextrin, maltodextrin, dextrose, calcium carbonate, calcium sulfate, dibasic calcium phosphate dihydrate, tribasic calcium phosphate, magnesium carbonate, magnesium oxide and combination thereof.

The binder used in pharmaceutical formulation include but not limited to acacia, guar gum, alginic acid, carbomer, dextrin, maltodextrin, methylcellulose, ethyl cellulose, hydroxyethyl cellulose, hydroxypropyl cellulose, hydroxypropyl methylcellulose, carboxymethylcellulose sodium, liquid glucose, magnesium aluminum silicate, polymethacrylates, povidone, copovidone, gelatin, starch and combination thereof.

The disintegrant used in pharmaceutical formulation include but not limited to methyl cellulose, microcrystalline cellulose, carboxymethyl cellulose calcium, carboxymethyl cellulose sodium, crospovidone, polacrilin potassium, starch, pregelatinized starch, sodium starch glycolate and combination thereof.

The compositions further include additional pharmaceutically acceptable excipients, including one or more of glidant like colloidal silicon dioxide, film forming agents like hypromellose, enteric coating polymers, lubricants like talc, magnesium stearate, sodium stearyl fumarate, surfactants such as sodium lauryl sulphate, and other commonly used excipients. This list, and the foregoing listings of representative specific excipients, is not intended to be exhaustive, as those skilled in the art will be aware of other substances that can be used.

Formulation of present invention may optionally include antioxidants including, but not limited to, ascorbic acid and its esters, butylated hydroxy toluene (BHT), butylated hydroxy anisole (BHA), a-tocopherol, cystein, citric acid, ascorbic acid, propyl gallate, and sodium bisulfite.

The ratio of active(s) to inactive(s) according to present invention is at least 1:1 or more. The preferable ratio of active(s) to inactive(s) according to present invention is about 1:2.5 or more.

The process for manufacturing the formulation as per present invention is not limited to the processes described in the application. The formulation can be prepared by using any of the processes known to one skilled in the art. One, or more than one, active ingredient can be used along with or without directly compressible grade excipients or granulated together or separately by wet granulation or dry granulation with or without excipients. Further one or more than one active(s) can be granulated while the others may be used as such without granulation.

In yet another embodiment, the pharmaceutical compositions of the present invention are manufactured as described below. The granules of active(s) are prepared by sifting the actives and excipients through the desired mesh size sieve and then are mixed using a rapid mixer granulator or planetary mixer or mass mixer or ribbon mixer or fluid bed processor or any other suitable device. The blend can be granulated, such as by adding a solution of a binder whether alcoholic or hydro-alcoholic or aqueous in a low or high shear mixer, fluidized bed granulator and the like or by dry granulation. The granulate can be dried using a tray drier or fluid bed drier or rotary cone vacuum drier and the like. The sizing of the granules can be done using an oscillating granulator or comminuting mill or any other conventional equipment equipped with a suitable screen. Alternatively, granules can be prepared by extrusion and spheronization, or roller compaction.

Also the manufacture of granules of actives can be made by mixing the directly compressible excipients or by roller compaction. The blend so obtained can be compressed using a suitable device, such as a station rotary machine to form slugs, which are passed through a mill or fluid energy mill or ball mill or colloid mill or roller mill or hammer mill and the like, equipped with a suitable screen to obtain the milled slugs of actives. The granules may optionally directly fill into a capsule.

In another aspect of the invention, the smaller tablets can be made by compressing the granules using die-and-punch of various sizes and shapes, as desired. Optionally, the coating on the tablets can be applied by techniques known to one skilled in the art such as spray coating, dip coating, fluidized bed coating and the like.

In one of the aspects of the present invention, a suitable solvent system such as alcoholic or hydroalcoholic or aqueous or organic may be used.

In another aspect of the invention, the tablets, pellets, granules, powder can be filled into capsules.

In another aspect of the invention tablets, pellets, granules and powder can be finally formulated into tablet dosage form like tablet-in-tablet, layered tablet, inlay tablet, multi-particulate tablet and the like. The tablet dosage form is optionally coated.

A further aspect the invention provides solid oral pharmaceutical composition comprising combination of HMG Coenzyme-A reductase inhibitor, adrenergic receptor blocking agent renin-angiotensin enzyme inhibitor, diuretic, platelet aggregation inhibitor and at least one pharmaceutically acceptable excipient, whereby the therapeutic effect achieved with the composition in the management of atherosclerosis is comparable, e.g. similar, to that achieved with the known separate formulations of HMG Coenzyme-A reductase inhibitor, adrenergic receptor blocking agent renin-angiotensin enzyme inhibitor, diuretic, platelet aggregation inhibitor, which are administered concomitantly, at the same doses of the active agents as the combination formulation of the invention.

In an embodiment of the combination composition of the invention, the composition is pharmacokinetically comparable to the known formulations, e.g. HMG Coenzyme-A reductase inhibitor, adrenergic receptor blocking agent, renin-angiotensin enzyme inhibitor, diuretic, platelet aggregation inhibitor formulations used herein as a reference, administered concomitantly at the same doses of active agents as the composition of the invention.

In a further embodiment, the composition of the invention is substantially bioequivalent with the known formulations, e.g. the bioavailability achieved with the composition of the invention is at levels comparable to that achieved with the concomitant administration of the same doses of the known separate formulations of HMG Coenzyme-A reductase inhibitor, adrenergic receptor blocking agent, renin-angiotensin enzyme inhibitor, diuretic, platelet aggregation inhibitor formulations used herein as a reference.

The following examples will further illustrate certain aspects of the invention in greater detail and are not intended to limit the scope of the invention.

EXAMPLES

I) The following is the example of multi-component active for the purpose of the invention.

A) Ramipril

Hydrochlorthiazide

Atenolol

Simvastatin

Aspirin

B) Atorvastatin

Nebivolol

Ramipril

Hydrochlorothiazide

Aspirin

II) Examples for formulation

Example 1 A

| S. No. | INGREDIENTS | Mg/Capsule |
|---|---|---|
| 1. | Atenolol | 50.00 |
| 2. | Ramipril | 5.00 |
| 3. | Hydrochlorothiazide | 12.50 |
| 4. | Simvastatin | 20.00 |
| 5. | Aspirin | 100.00 |
| 6. | Microcrystalline Cellulose (Avicel pH 200) | 100.00 |
| 7. | Magnesium Stearate | 2.50 |
| | Total | 290.00 |

Manufacturing Process:

1. The active ingredient from S.No. 1 to 7 were mixed well and filled into hard gelatin capsule.

The composition of Example 1A was found to be unstable.

Example 1 B

Following is the example of Multi Component Composition which was found to be stable for one month but not in long term.

| S. No. | INGREDIENTS | Mg/Capsule |
|---|---|---|
| | Part A: Dry Blend | |
| 1 | Atorvastatin Calcium | 10.93 |
| 2 | Nebivolol Hydrochloride | 2.74 |
| 3 | Ramipril Hydrochloride | 5.00 |
| 4 | Hydrochlorothiazide | 12.74 |
| 5 | Pregelatinised Starch | 198.45 |
| 6 | Lactose (Direct Compression Grade) | 112.04 |
| 7 | Sodium Stearyl Fumarate | 4.00 |
| 8 | Sodium Lauryl Sulphate | 4.00 |
| | Part B: Aspirin Enteric Coated Tablets | |
| | I) Aspirin Core Tablet | |
| 1 | Aspirin Granules | 100.00 |
| 2 | Sodium Starch Glycolate | 13.00 |
| 3 | Microcrystalline Cellulose (Avicel pH 200) | 20.00 |
| 4 | Colloidal Silicon Dioxide | 2.00 |
| 5 | Sodium Stearyl Fumarate | 2.00 |
| | II) Seal Coating of Aspirin Core Tablet | |
| 1 | Hypromellose -5 cps | 3.51 |
| 2 | Poly Ethylene Glycol 6000 | 0.16 |
| 3 | Isopropyl Alcohol | q.s |
| 4 | Calcium Carbonate | 0.07 |
| 5 | Talc | 0.35 |
| 6 | *Isopropyl Alcohol 35% | q.s |
| 7 | *Methylene Chloride 65% | q.s |
| | III) Enteric Coating of Aspirin Seal Coated Tablet | |
| 1 | Methacrylic Acid co-polymer | 13.89 |
| 2 | *Isopropyl Alcohol | q.s |

*doesn't remain in final formulation

The blend from Part A and enteric coated tablet of aspirin from part B were filled in hard gelatin capsule.

Example 1B was found to be stable for one month but not in long term.

Example 1 C

| S. No. | INGREDIENTS | Mg/Capsule |
|---|---|---|
| | Part A: Aspirin Enteric Coated Tablets | |
| | I) Aspirin Core Tablet | |
| 1 | Aspirin Granules | 100.25 |
| 2 | Sodium Starch Glycolate | 13.00 |
| 3 | Microcrystalline Cellulose (Avicel PH 200) | 20.00 |
| 4 | Colloidal Silicon Dioxide | 2.00 |
| 5 | Sodium Stearyl Fumarate | 2.00 |
| | II) Seal Coating of Aspirin Core Tablet | |
| 1 | Hypromellose -5 cps | 3.15 |
| 2 | Poly Ethylene Glycol 6000 | 0.15 |
| 3 | Isopropyl Alcohol | q.s |
| 4 | Calcium Carbonate | 0.06 |
| 5 | Talc | 0.31 |
| 6 | *Isopropyl Alcohol 35% | q.s |
| 7 | *Methylene Chloride 65% | q.s |
| | III) Enteric Coating of Aspirin Seal Coated Tablet | |
| 1 | Eudragit L30 D-55 | 10.03 |
| 2 | Triethyl Citrate | 0.35 |
| 3 | Talc | 0.90 |
| 4 | *Water | q.s |
| | Part B: Dry Blend | |
| 1 | Simvastatin | 20.00 |
| 2 | Ramipril | 5.00 |
| 3 | Atenolol | 50.00 |
| 4 | Hydrochlorothiazide | 12.50 |

*doesn't remain in final formulation

Manufacturing Process:
Part A: Aspirin Enteric Coated Tablets
1. Aspirin granules, Sodium starch glycolate, microcrystalline cellulose, Colloidal silicon dioxide and sodium Stearyl Fumarate were used to manufacture core tablets of Aspirin. The tablets were manufactured by direct compression.
2. The Aspirin core tablets were seal coated.
3. The Seal coated aspirin tablets were enteric coated.

Part B: Dry Blend:
1. Simvastatin, Ramipril, Atenolol, and Hydrochlorothiazide were sifted and mixed thoroughly.

The enteric coated tablet of aspirin from part A and blend from Part B were filled in hard gelatin capsule.

The composition of Example 1C was found to be unstable.

Example 2

The following are examples of unstable pharmaceutical compositions wherein one of the active ingredients was incorporated as a table as per below:

Example 2A: Simvastatin Tablet

| S. No | Ingredients | Mg/Tablet |
|---|---|---|
| | Core Tablet | |
| 1. | Simvastatin | 20.00 |
| 2. | Butyl Hydroxy Anisole | 0.04 |
| 3. | Ascorbic Acid | 5.00 |
| 4. | Citric Acid Monohydrate | 2.50 |
| 5. | Lactose Monohydrate | 100.46 |
| 6. | Starch 1500 | 10.00 |
| 7. | Microcrystalline Cellulose (MCC PH200) | 10.00 |
| 8. | Talc | 1.00 |
| 9. | Magnesium Stearate | 3.00 |
| | Core Tablet Weight | 152.00 |
| | Film Coating | |
| 1. | Opadry brown | 4.56 |
| 2. | Purified Water | q.s |
| | Coated Tablet Weight | 156.56 |

Manufacturing Process:
1. Sift Simvastatin, Lactose monohydrate, Colloidal silicon dioxide, Ascorbic acid, Citric acid through 40# and granulate with IPA-BHA solution.
2. Dry the granules to get the LOD below 3.0% w/w.
3. Mill Sift the dried granules through 40#.
4. Sift Starch 1500, Avicel PH 200, Aerosil and Talc through 40# and mix with above blend for 10 minutes.
5. Lubricate the above blend by mixing with Magnesium Stearate for 5 minutes.
6. Compress the above lubricated blend into tablets.
7. Film coat the compressed tablets with Opadry Brown.

The composition of Example 2A was found to be unstable in Multi-constituent pharmaceutical composition.

Example 2B: Atenolol Tablet

| S. No | Ingredients | Mg/Tablet |
|---|---|---|
| | Core Tablet | |
| 1. | Atenolol | 50.00 |
| 2. | Microcrystalline cellulose (Avicel Ph 101) | 33.50 |
| 3. | Sodium Starch Glycholate | 5.00 |
| 4. | Polyvinyl pyrrolidone, PVPK 30 | 7.50 |
| 5. | Water | qs |
| 6. | Magnesium Stearate | 1.5 |
| | Film Coating | |
| 1. | Opadry yellow | 3.00 |
| 2. | Purified Water | qs |
| | Total weight | 105.00 |

The composition of Example 2B was found to be unstable in multi-constituent pharmaceutical composition.

Example 2C: Aspirin Tablet

| S. No | Ingredients | Mg/Tablet |
|---|---|---|
| | Core | |
| 1. | Aspirin Granules | 100.00 |
| 2. | Sodium Starch Glycolate | 13.0 |
| 3. | Microcrystalline cellulose (Avicel PH 200) | 20.0 |
| 4. | Sodium Stearyl Fumarate | 2.0 |
| 5. | Silicon Dioxide (Aerosil 200) | 2.0 |
| | Coat I | |
| 1. | Hydroxypropyl methyl cellulose (HPMC-5 cps) | 3.0 |
| 2. | Polyethylene Glycol (PEG 6000) | 0.5 |
| 3. | Isopropyl Alcohol (IPA) | Qs |
| 4. | Calcium Carbonate | 0.8 |

-continued

| S. No | Ingredients | Mg/Tablet |
|---|---|---|
| 5. | Talc | 4.0 |
| 6. | Isopropyl Alcohol (IPA) | Qs |
| 7. | Methylene Dichloride (MDC) | Qs |
| | Coat II | |
| 1. | Methacrylate polymer (Eudragit L30 D55) | 11.0 |
| 2. | Triethyl citrate | 2.0 |
| 3. | Talc | 3.0 |
| 4. | Purified Water | Qs |
| | Total weight | 161.3 |

Manufacturing Process:
Tablet Compression
1. Sift Sodium Starch Glycolate, Avicel PH-200 & Aerosil 200 through sieve #40 using mechanical sifter.
2. Mix the above blend to aspirin granules and transfer the blend to double cone blender and lubricate the blend with sodium stearyl fumarate passed through sieve #40 for 15 minutes.
3. Compress the blend using suitable punch.

Seal Coating
1. Take HPMC disperse in mix of IPA/MDC.
2. Homogenized Talc, Ca-Carbonate in IPA/MDC (35:65) for 5-10 minutes, transfer it into solution.1 (Solution A)
3. Dissolve PEG6000 in Hot IPA for 5-10 mins, transfer it in to Solution A
4. Pass the dispersion through #60, continue the stirring.
5. Seal coat the core tablets Enteric Coating
1. Homogenized Talc in Purified water for 5-10 minutes solution.1.
2. After cooling soln.1 transfer it in to Eudragit L30D-55, stir it for 5-10 minutes add Triethyl citrate (TEC) stir it for 5-10 minutes.
3. Pass solution through #60-80 mesh & continue stirring during.
4. Enteric coat the seal coated tablet The composition of Example 2C was found to be unstable.

Example 3

Example of individual tablets which were found stable when incorporated in multi-component pharmaceutical composition. These examples illustrate certain aspects of the invention in greater detail and are not intended to limit the scope of the invention.

Example 3A: Simvastatin Tablet

| S. No. | Ingredients | Mg/Tablet |
|---|---|---|
| 1. | Simvastatin | 20.00 |
| 2. | Lactose monohydrate (Pharmatose 200 M) | 94.00 |
| 3. | Silicon dioxide (Aerosil) | 1.00 |
| 4. | Butylated Hydroxy Anisole | 0.07 |
| 5. | Isopropyl alcohol | qs |
| 6. | Pregelatinised Starch 1500 | 5.00 |
| 7. | Microcrystalline cellulose (Avicel PH 200) | 20.13 |
| 8. | Silicon dioxide (Aerosil) | 2.40 |
| 9. | Talc | 1.20 |
| 10. | Magnesium Stearate | 1.20 |

| S. No. | Ingredients | Mg/Tablet |
|---|---|---|
| | Film Coating | |
| 1. | Opadry Brown | 4.00 |
| 2. | Purified Water | qs |
| | Total weight | 149.00 |

The pharmaceutical composition incorporating above tablet was found to be stable at accelerated conditions, which is equivalent to a shelf life of more then 24 months.

Example 3.B(i): Atenolol Tablet

| S. No. | Ingredients | Mg/Tablet |
|---|---|---|
| | Core | |
| 1. | Atenolol | 50.00 |
| 2. | Microcrystalline cellulose (Avicel pH 200) | 35.50 |
| 3. | Sodium steryl glycolate | 10.00 |
| 4. | Silicon dioxide (Aerosil) | 1.50 |
| 5. | Magnesium Stearate | 5.00 |
| 6. | Isopropyl alcohol | qs |
| | Film Coating | |
| 1. | Opadry yellow | 3.00 |
| 2. | Purified Water | qs |
| | Total weight | 105.00 |

Example 3.B(ii): Atenolol Tablet

| S. No | INGREDIENTS | Mg/Tablet |
|---|---|---|
| 1. | Atenolol | 50.00 |
| 2. | Sunset Yellow lake | 0.02 |
| 3. | Microcrystalline Cellulose (Avicel PH 200) | 36.00 |
| 4. | Sodium Stearyl Glycolate | 10.00 |
| 5. | Colloidal Silicon Dioxide | 1.50 |
| 6. | Magnesium Stearate | 5.00 |
| | Total | 102.52 |

The pharmaceutical composition incorporating above tablet was found to be stable at accelerated conditions, which is equivalent to a shelf life of more then 24 months.

Example 3C(i): Aspirin Tablet

| S. No | Ingredients | Mg/Tablet |
|---|---|---|
| | Core | |
| 1. | Aspirin | 100.0 |
| 2. | Pregelatinised Starch (Starch 1500) | 4.35 |
| 3. | Microcrystalline cellulose (Avicel PH 200) | 8.5 |
| 4. | Sodium Lauryl Sulphate | 0.15 |
| 5. | Silicon dioxide (Aerosil 200) | 3.00 |
| | Coat I | |
| 1. | Ethyl cellulose 7 cps | 0.45 |
| 2. | Hydroxypropyl methylcellulose (HPMC 5 CPS) | 1.90 |
| 3. | Isopropyl Alcohol | QS |

-continued

| S. No | Ingredients | Mg/Tablet |
|---|---|---|
| 4. | Methylene Dichloride | QS |
| 5. | Propylene glycol | 0.15 |
| | Coat II | |
| 1. | Hydroxypropyl methylcellulose Pthalate Pink | 11.89 |
| 2. | Isopropyl Alcohol | QS |
| 3. | Methylene Dichloride | QS |
| | Coat III | |
| 1. | Insta moist shield | 2.61 |
| 2. | Isopropyl Alcohol | QS |
| 3. | Methylene Dichloride | QS |
| | Total weight | 133.00 |

Example 3C(ii): Enteric Coated Aspirin Tablet

| Sr. No | Ingredients | Mg/Tablet |
|---|---|---|
| I. | Core Tablet | |
| 1. | Aspirin granules | 100.00 |
| 2. | Pregelatinized Starch (Starch 1500) | 8.00 |
| 3. | Microcrystalline Cellulose (Avicel PH 200) | 8.00 |
| 4. | Sodium lauryl sulphate | 0.15 |
| 5. | Colloidal Silicon Dioxide (Aerosil 200) | 0.15 |
| | Total | 116.30 |
| II. | SEAL COAT (~3.5% Weight gain) | |
| 1. | Hypromellose - 5 cps | 2.80 |
| 2. | Dibutyl Phthalate | 0.28 |
| 3. | Isopropyl Alcohol | q.s |
| 4. | Dichloromethane | q.s |
| | Total(I + II) | 119.38 |
| III. | ENTERIC COAT (~10% Weight Gain) | |
| 1. | Methacrylic Acid Copolymer (Type A) | 9.55 |
| 2. | Isopropyl Alcohol | q.s |
| 3. | Dichloromethane | q.s |
| | Total (I + II + III) | 128.93 |
| IV. | PROTECTIVE COAT (~2% Weight Gain) | |
| 1. | Insta Moist Sheild ® | 2.61 |
| 2. | Isopropyl Alcohol | q.s |
| 3. | Dichloromethane | q.s |
| | Total (I + II + III + IV) | 131.54 |

Manufacturing Process:
Tablet Compression
1. Sift Aspirin through 20# and Starch 1500, Avicel PH-200, SLS & Aerosil through sieve #40 using mechanical sifter.
2. Mix the above blend in double cone blender for 15 minutes.
3. Compress the blend using 6 mm punch.

Seal Coating (Coat I)
1. Take Ethyl Cellulose and HPMC, disperse in mixture of IPA/MDC under continuous stirring. Add propylene glycol to the dispersion.
2. Coat the tablets with the above seal coating material to achieve the required weight gain.

Enteric Coating (Coat II)
1. Disperse HPMC P in mixture of IPA/MDC under continuous stirring.
2. Coat the tablets with the above coating material to achieve the required weight gain.

Protective Coating (Coat III)
1. Disperse Instamoist shield in mixture of IPA/MDC under continuous stirring.
2. Coat the tablets with the above coating material to achieve the required weight gain.

The pharmaceutical composition incorporating above tablet was found to be stable at accelerated conditions, which is equivalent to a shelf life of more then 24 months.

Example 4

Following are the examples of granules and blend which found to be stable when incorporated in multi-component pharmaceutical composition. These examples illustrate certain aspects of the invention in greater detail and are not intended to limit the scope of the invention.

Example 4A: Simvastatin Granules

| Sr. No | Ingredients | Mg |
|---|---|---|
| 1. | Simvastatin | 20.00 |
| 2. | Lactose anhydrous(Pharmatose DCL 21) | 99.42 |
| 3. | Pregelatinised Starch (Starch 1500) | 10.00 |
| 4. | Silicon dioxide (Aerosil) | 0.50 |
| 5. | Butylated Hydroxy Anisole | 0.08 |
| 6. | Isopropyl alcohol | qs |
| | Total | 130.00 |

Example 4B: Atenolol Granules

| Sr. No. | Ingredients | Mg |
|---|---|---|
| 1. | Atenolol | 50.00 |
| 2. | Microcrystalline cellulose (Avicel PH 101) | 77.00 |
| 3. | Polyvinylpyrrolidone (PVP K 29/32) | 3.00 |
| 4. | Isopropyl alcohol | qs |
| | Total | 130.00 |

Example 4C: Ramipril Granules

| S. No | Ingredients | Mg |
|---|---|---|
| 1. | Ramipril | 5.00 |
| 2. | Hydroxypropyl methylcellulose (HPMC 5 cps) | 0.20 |
| 3. | Isopropyl Alcohol | qs |
| 4. | Dichloromethane | qs |
| | Total | 5.20 |

Example 4D: Hydrochlorothiazide Blend

| S. No | Ingredients | Mg |
|---|---|---|
| 1. | Hydrochlorothiazide | 12.50 |
| 2. | Lactose (Pharmatose DCL 21) | 90.00 |
| 3. | Pregelatinised Starch (Starch 1500) | 52.50 |
| | Total | 155.00 |

Example 5

Following are examples of Multi Component Composition incorporating tablet, granules and/or blend which were found unstable.

Example 5A

| S. No | Ingredients | Mg/Capsule |
|---|---|---|
| | Part A | |
| 1. | Atenolol Tablet from example 2B equivalent to Atenolol | 50.00 |
| | Part B | |
| 1. | Simvastatin granules from example 4A equivalent to Simvastatin | 20.00 |
| 2. | Ramipril granules from example 4C equivalent to Ramipril | 5.00 |
| 3. | Hydrochlorothiazide Blend from example 4D equivalent to HCTZ | 12.50 |

Part B was lubricated with sodium stearyl fumarate (2.00 mg/Capsule) and aerosil (2.00 mg/Capsule) for 5 min. and filled the tablets from Part A, and blend from Part B in hard gelatin capsule.

Example 5B

| S. No | Ingredients | Mg/Capsule |
|---|---|---|
| | Part A | |
| 1. | Simvastatin Tablet from example 2A equivalent to Simvastatin | 20.00 |
| | Part B | |
| 1. | Atenolol granules from Example 4B equivalent to Atenolol | 50.00 |
| 2. | Ramipril granules from example 4C equivalent to Ramipril | 5.00 |
| 3. | Hydrochlorothiazide Blend from example 4D equivalent to HCTZ | 12.50 |

Part B was lubricated with Sodium Stearyl Fumarate (2.00 mg/Capsule) and Aerosil (2.00 mg/Capsule) for 5 min. and filled the tablets from Part A, and blend from Part B in hard gelatin capsule.

Example 5C

| S. No | Ingredients | Mg/Capsule |
|---|---|---|
| | Part A | |
| 1. | Simvastatin Tablet from example 2A equivalent to Simvastatin | 20.00 |
| | Part B | |
| 1. | Atenolol Tablet from example 2B equivalent to Atenolol | 50.00 |
| | Part C | |
| 1. | Ramipril granules from example 4C equivalent to Ramipril | 5.00 |
| 2. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A, Part B, and blend from Part C in hard gelatin capsule.

Example 5D

| S. No | Ingredients | Mg/Capsule |
|---|---|---|
| | Part A | |
| 1. | Atenolol Tablet from example 2B equivalent to Atenolol | 50.00 |
| | Part B | |
| 1. | Aspirin Tablet from example 2C equivalent to Aspirin | 100.00 |
| | Part C | |
| 1. | Simvastatin granules from example 4A equivalent to Simvastatin | 20.00 |
| 2. | Ramipril granules from example 4C equivalent to Ramipril | 5.00 |
| 3. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A and B, and blend from Part C in hard gelatin capsule.

Example 5E

| S. No | Ingredients | Mg/Capsule |
|---|---|---|
| | Part A | |
| 1. | Simvastatin Tablet from example 2A equivalent to Simvastatin | 20.00 |
| | Part B | |
| 1 | Aspirin Tablet from example 2C equivalent to Aspirin | 100.00 |
| | Part C | |
| 1. | Atenolol granules from Example 4B equivalent to Atenolol | 50.00 |
| 2. | Ramipril granules from example 4C equivalent to Ramipril | 5.00 |
| 3. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A and B, and blend from Part C in hard gelatin capsule.

Example 5F

| S. No | Ingredients | Mg/Capsule |
|---|---|---|
| | Part A | |
| 1. | Simvastatin Tablet from example 2A equivalent to Simvastatin | 20.00 |
| | Part B | |
| 1. | Atenolol Tablet from example 2B equivalent to Atenolol | 50.00 |
| | Part C | |
| 1. | Aspirin Tablet from example 2C equivalent to Aspirin | 100.00 |
| | Part D | |
| 1. | Ramipril granules from example 4C equivalent to Ramipril | 5.00 |
| 2. | Hydrochlorothiazide Blend from example 4D equivalent to HCTZ | 12.50 |

Part D was lubricated with Sodium Stearyl Fumarate (2.00 mg/Capsule) and Aerosil (2.00 mg/Capsule) for 5 min. and filled the tablets from Part A, Part B, C and blend from Part D in hard gelatin capsule.

Example 6

Following are examples of stable Multi Component Composition incorporating tablet and/or granules from example 3&4. The following examples illustrate certain aspects of the invention in greater detail and are not intended to limit the scope of the invention.

Example 6A

| S. No | Ingredients | Mg/Capsule |
|---|---|---|
| | Part A | |
| 1. | Atenolol Tablet from Example 3B(i) equivalent to Atenolol | 50.00 |
| | Part B | |
| 1. | Simvastatin granules from example 4A equivalent to Simvastatin | 20.00 |
| 2. | Ramipril granules from example 4C equivalent to Ramipril | 5.00 |
| 3. | Hydrochlorothiazide Blend from example 4D equivalent to HCTZ | 12.50 |

Part B was lubricated with Sodium Stearyl Fumarate (2.00 mg/Capsule) and Aerosil (2.00 mg/Capsule) for 5 min. and filled the tablets from Part A, and blend from Part B in hard gelatin capsule.

Example 6B

| S. No | Ingredients | Mg/Capsule |
|---|---|---|
| | Part A | |
| 1. | Simvastatin Tablet from example 3A equivalent to Simvastatin | 20.00 |
| | Part B | |
| 1. | Atenolol granules from Example 4B equivalent to Atenolol | 50.00 |
| 2. | Ramipril granules from example 4C equivalent to Ramipril | 5.00 |
| 3. | Hydrochlorothiazide Blend from example 4D equivalent to HCTZ | 12.50 |

Part B was lubricated with Sodium Stearyl Fumarate (2.00 mg/Capsule) and Aerosil (2.00 mg/Capsule) for 5 min. and filled the tablets from Part A, and blend from Part B in hard gelatin capsule.

Example 6C

| S. No | Ingredients | Mg/Capsule |
|---|---|---|
| | Part A | |
| 1. | Atenolol Tablet from Example 3B(i) equivalent to Atenolol | 50.00 |
| | Part B | |
| 1. | Simvastatin Tablet from Example 3A equivalent to Simvastatin | 20.00 |
| | Part C | |
| 1. | Ramipril granules from example 4C equivalent to Ramipril | 5.00 |
| 2. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A, Part B, and blend from Part C in hard gelatin capsule.

Example 6D

| S. No | Ingredients | Mg/Capsule |
|---|---|---|
| | Part A | |
| 1. | Atenolol Tablet from Example 3B(i) equivalent to Atenolol | 50.00 |
| | Part B | |
| 1. | Aspirin Tablet from example 3C(i) equivalent to Aspirin | 100.00 |
| | Part C | |
| 1. | Simvastatin granules from example 4A equivalent to Simvastatin | 20.00 |
| 2. | Ramipril granules from example 4C equivalent to Ramipril | 5.00 |
| 3. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A and B, and blend from Part C in hard gelatin capsule.

Example 6E

| S. No | Ingredients | Mg/Capsule |
|---|---|---|
| | Part A | |
| 1. | Simvastatin Tablet from Example 3A equivalent to Simvastatin | 20.00 |
| | Part B | |
| 1. | Aspirin Tablet from example 3C(i) equivalent to Aspirin | 100.00 |
| | Part C | |
| 1. | Atenolol granules from Example 4B equivalent to Atenolol | 50.00 |
| 2. | Ramipril granules from example 4C equivalent to Ramipril | 5.00 |
| 3. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A and B, and blend from Part C in hard gelatin capsule.

Example 6F

| S. No | Ingredients | Mg/Capsule |
|---|---|---|
| | Part A | |
| 1. | Atenolol Tablet from Example 3B(i) equivalent to Atenolol | 50.00 |
| | Part B | |
| 1. | Simvastatin Tablet from Example 3A equivalent to Simvastatin | 20.00 |
| | Part C | |
| 1. | Aspirin Tablet from example 3C(i) equivalent to Aspirin | 100.00 |
| | Part D | |
| 1. | Ramipril granules from example 4C equivalent to Ramipril | 5.00 |
| 2. | Hydrochlorothiazide Blend from example 4D equivalent to HCTZ | 12.50 |

Part D was lubricated with Sodium Stearyl Fumarate (2.00 mg/Capsule) and Aerosil (2.00 mg/Capsule) for 5 min. and filled the tablets from Part A, Part B, C and blend from Part D in hard gelatin capsule.

Example 6G

| S. No | Ingredients | Mg/Capsule |
|---|---|---|
| | Part A | |
| 1. | Aspirin Enteric coated Tablet from Example 3C(i) equivalent to Aspirin | 100.00 |
| | Part B | |
| 1. | Atenolol | 50.00 |
| 2. | Ramipril | 5.00 |
| 3. | Hydrochlorothiazide | 12.50 |
| 4. | Simvastatin | 20.00 |
| 5. | Butyl Hydroxy Anisole | 0.04 |
| 6. | Sodium Lauryl Sulphate | 2.50 |
| 7. | Sodium Stearyl Fumarate | 2.00 |
| 8. | Pregelatinised Starch (Starch 1500) | 320.00 |

The blend from Part B and enteric coated tablet from part A were filled in hard gelatin capsule.

Example 6H

| S. No | Ingredients | Mg/Capsule |
|---|---|---|
| | Part A | |
| 1. | Aspirin Enteric coated Tablet from Example 3C(i) equivalent to Aspirin | 100.00 |
| | Part B | |
| 1. | Atenolol | 50.00 |
| 2. | Ramipril | 5.00 |
| 3. | Hydrochlorothiazide | 12.50 |
| 4. | Simvastatin | 20.00 |
| 5. | Butyl Hydroxy Anisole | 0.04 |
| 6. | Citric Acid | 2.50 |
| 7. | Ascorbic Acid | 5.00 |
| 8. | Sodium Lauryl Sulphate | 2.50 |
| 9. | Sodium Stearyl Fumarate | 2.00 |
| 10. | Pregelatinised Starch (Starch 1500) | 312.50 |

The blend from Part B and Enteric Coated Tablet from Part A were filled in hard gelatin capsule.

Example 6I

| S. No | Ingredients | Mg/Capsule |
|---|---|---|
| | Part A | |
| 1. | Atenolol Tablet from Example 3B(i) equivalent to Atenolol | 50.00 |
| | Part B | |
| 1. | Aspirin Enteric coated Tablet from Example 3C(i) equivalent to Aspirin | 100.00 |
| | Part C | |
| 1. | Ramipril | 5.00 |
| 2. | Hydrochlorothiazide | 12.50 |
| 3. | Simvastatin | 20.00 |
| 4. | Butyl Hydroxy Anisole | 0.04 |
| 5. | Sodium Lauryl Sulphate | 2.50 |
| 6. | Sodium Stearyl Fumarate | 2.00 |
| 7. | Pregelatinised Starch (Starch 1500) | 270.00 |

The tablets from Part A, Part B and blend from Part C were filled in hard gelatin capsule.

Example 6J

| S. No | Ingredients | Mg/Capsule |
|---|---|---|
| | Part A | |
| 1. | Atenolol Tablet from Example 3B(ii) equivalent to Atenolol | 50.00 |

-continued

| S. No | Ingredients | Mg/Capsule |
|---|---|---|
| | Part B | |
| 1. | Aspirin Enteric coated Tablet from Example 3C(i) equivalent to Aspirin | 100.00 |
| | Part C | |
| 1. | Ramipril | 5.00 |
| 2. | Hydrochlorothiazide | 12.50 |
| 3. | Simvastatin | 20.00 |
| 4. | Butyl Hydroxy Anisole | 0.04 |
| 5. | Citric Acid | 2.50 |
| 6. | Ascorbic Acid | 5.00 |
| 7. | Sodium Lauryl Sulphate | 2.50 |
| 8. | Sodium Stearyl Fumarate | 2.00 |
| 9. | Pregelatinised Starch (Starch 1500) | 262.50 |

The tablets from Part A, Part B and blend from Part C were filled in hard gelatin capsule.

Example 6K

Atenolol Tablet coated with Ramipril and granules of simvastatin and blend of Hydrochlorothiazide

| S. No | Ingredients | Mg/Capsule |
|---|---|---|
| | Part A | |
| 1. | Atenolol Tablet from Example 3B(i) equivalent to Atenolol | 50.00 |
| | Part B (Ramipril coating) | |
| 1. | Ramipril | 5.00 |
| 2. | HPMC 5 cps | 5.00 |
| 3. | Sodium Bicarbonate | 5.00 |
| 4. | Purified Water | qs |
| | Seal coating | |
| 1. | HPMC 5 cps | 1.15 |
| 2. | Sodium Bicarbonate | 0.30 |
| | Total wt. of coated tablet | 122.00 |
| | Part C | |
| 1. | Simvastatin granules from example 4A equivalent to Simvastatin | 20.00 |
| 2. | Hydrochlorothiazide Blend from example 4D equivalent to HCTZ | 12.50 |

Example 6L

| S. No | Ingredients | Mg/Capsule |
|---|---|---|
| | Part A | |
| 1. | Aspirin Enteric coated Tablet from Example 3C(ii) equivalent to Aspirin | 100.00 |
| | Part B | |
| 1. | Simvastatin | 20.00 |
| 2. | Atenolol | 50.00 |
| 3. | Ramipril | 5.00 |
| 4. | Hydrochlorothiazide | 12.50 |
| 5. | Butyl Hydroxy Anisole | 0.04 |
| 6. | Sodium Lauryl Sulphate | 2.50 |
| 7. | Sodium Stearyl Fumarate | 2.00 |
| 8. | Pregelatinised Starch (Starch 1500) | 320.00 |

The blend from Part B and Enteric Coated Tablet from Part A were filled in hard gelatin capsule.

Example 6M

| S. No | Ingredients | Mg/Capsule |
|---|---|---|
| | Part A | |
| 1. | Aspirin Enteric coated Tablet from Example 3C(ii) equivalent to Aspirin | 100.00 |
| | Part B | |
| 1. | Simvastatin | 20.00 |
| 2. | Atenolol | 50.00 |
| 3. | Ramipril | 5.00 |
| 4. | Hydrochlorothiazide | 12.50 |
| 5. | Butyl Hydroxy Anisole | 0.04 |
| 6. | Citric Acid | 2.50 |
| 7. | Ascorbic Acid | 5.00 |
| 8. | Sodium Lauryl Sulphate | 2.50 |
| 9. | Sodium Stearyl Fumarate | 2.00 |
| 10. | Pregelatinised Starch (Starch 1500) | 312.50 |

The blend from Part B and Enteric Coated Tablet from Part A were filled in hard gelatin capsule.

Example 6N

| S. No | Ingredients | Mg/Capsule |
|---|---|---|
| | Part A | |
| 1. | Aspirin Enteric coated Tablet from Example 3C(ii) equivalent to Aspirin | 100.00 |
| | Part B | |
| 1. | Atenolol Tablet from Example 3B(ii) equivalent to Atenolol | 50.00 |
| | Part C | |
| 1. | Simvastatin | 20.00 |
| 2. | Ramipril | 5.00 |
| 3. | Hydrochlorothiazide | 12.50 |
| 4. | Butyl Hydroxy Anisole | 0.04 |
| 5. | Sodium Lauryl Sulphate | 2.50 |
| 6. | Sodium Stearyl Fumarate | 2.00 |
| 7. | Pregelatinised Starch (Starch 1500) | 270.00 |

The tablets from Part A, Part B and blend from Part C were filled in hard gelatin capsule.

Example 6O

| S. No | Ingredients | Mg/Capsule |
|---|---|---|
| | Part A | |
| 1. | Aspirin Enteric coated Tablet from Example 3C(ii) equivalent to Aspirin | 100.00 |
| | Part B | |
| 1. | Atenolol Tablet from Example 3B(ii) equivalent to Atenolol | 50.00 |
| | Part C | |
| 1. | Simvastatin | 20.00 |
| 2. | Ramipril | 5.00 |
| 3. | Hydrochlorothiazide | 12.50 |
| 4. | Butyl Hydroxy Anisole | 0.04 |
| 5. | Citric Acid | 2.50 |

-continued

| S. No | Ingredients | Mg/Capsule |
|---|---|---|
| 6. | Ascorbic Acid | 5.00 |
| 7. | Sodium Lauryl Sulphate | 2.50 |
| 8. | Sodium Stearyl Fumarate | 2.00 |
| 9. | Pregelatinised Starch (Starch 1500) | 262.50 |

The tablets from Part A, Part B and blend from Part C were filled in hard gelatin capsule.

Example 6P

| S. No | Ingredients | Mg/Capsule |
|---|---|---|
| | Part A | |
| 1. | Atenolol Tablet is prepared as per example 3B(i) wherein Atenolol | 100.00 |
| | Part B | |
| 1. | Simvastatin Tablet from Example 3A equivalent to Simvastatin | 20.00 |
| | Part C | |
| 1. | Aspirin Tablet from example 3C(i) equivalent to Aspirin | 50.00 |
| | Part D | |
| 1. | Ramipril granules from example 4C equivalent to Ramipril | 10.00 |
| 2. | Hydrochlorothiazide Blend from example 4D equivalent to HCTZ | 12.50 |

Part D was lubricated with Sodium Stearyl Fumarate (2.00 mg/Capsule) and Aerosil (2.00 mg/Capsule) for 5 min. and filled the tablets from Part A, Part B, C and blend from Part D in hard gelatin capsule.

Example 6Q

| S. No | Ingredients | Mg/Capsule |
|---|---|---|
| | Part A | |
| 1. | Atenolol Tablet from example 3B(i) equivalent to Atenolol | 100.00 |
| | Part B | |
| 1. | Simvastatin Tablet from Example 3A equivalent to Simvastatin | 40.00 |
| | Part C | |
| 1. | Aspirin Tablet from example 3C(i) equivalent to Aspirin | 100.00 |
| | Part D | |
| 1. | Ramipril granules from example 4C equivalent to Ramipril | 10.00 |
| 2. | Hydrochlorothiazide Blend from example 4D equivalent to HCTZ | 25.00 |

Part D was lubricated with Sodium Stearyl Fumarate (2.00 mg/Capsule) and Aerosil (2.00 mg/Capsule) for 5 min. and filled the tablets from Part A, Part B, C and blend from Part D in hard gelatin capsule.

Example 6R

| S. No | Ingredients | Mg/Capsule |
|---|---|---|
| | Part A | |
| 1. | Atenolol Tablet from Example 3B(i) equivalent to Atenolol | 100.00 |
| | Part B | |
| 1. | Simvastatin Tablet from Example 3A equivalent to Simvastatin | 20.00 |
| | Part C | |
| 1. | Ramipril granules from example 4C equivalent to Ramipril | 5.00 |
| 2. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A, Part B, and blend from Part C in hard gelatin capsule.

Example 6S

| S. No | Ingredients | Mg/Capsule |
|---|---|---|
| | Part A | |
| 1. | Atenolol Tablet from Example 3B(i) equivalent to Atenolol | 50.00 |
| | Part B | |
| 1. | Simvastatin Tablet from Example 3A equivalent to Simvastatin | 40.00 |
| | Part C | |
| 1. | Ramipril granules from example 4C equivalent to Ramipril | 5.00 |
| 2. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A, Part B, and blend from Part C in hard gelatin capsule.

Example 6T

| S. No | Ingredients | Mg/Capsule |
|---|---|---|
| | Part A | |
| 1. | Atenolol Tablet from Example 3B(i) equivalent to Atenolol | 50.00 |
| | Part B | |
| 1. | Simvastatin Tablet from Example 3A equivalent to Simvastatin | 20.00 |
| | Part C | |
| 1. | Ramipril granules from example 4C equivalent to Ramipril | 2.50 |
| 2. | Hydrochlorothiazide Blend from example 4D equivalent to HCTZ | 12.50 |

Part C was lubricated with Sodium Stearyl Fumarate (2.00 mg/Capsule) and Aerosil (2.00 mg/Capsule) for 5 min. and filled the tablets from Part A, Part B, and blend from Part C in hard gelatin capsule.

Example 6U

| S. No. | Ingredients | Quantity (mg/cap.) |
|---|---|---|
| | Simvastatin Tablet | |
| 1. | Simvastatin | 20.0 |
| 2. | Colloidal Silicondioxide | 1.00 |
| 3. | Pregelatinised Starch (Starch 1500) | 10.0 |
| 4. | Butylated Hydroxy Anisole | 0.06 |
| 5. | Lactose anhydrous (DCL21) | 93.40 |
| 6. | Microcrystalline Cellulose (Avicel PH 200 ®) | 20.14 |
| 7. | Isopropyl Alcohol | QS |
| 8. | Talc | 1.20 |
| 9. | Magnesium stearate | 1.20 |
| 10. | Opadry Brown | 3.00 |
| 11. | Water | QS |
| | Tablet Weight | 150.00 |
| | Atenolol + Ramipril + HCTZ Granules | |
| 1. | Atenolol | 50.00 |
| 2. | Microcrystalline Cellulose (Avicel PH 101) | 77.00 |
| 3. | Poly Vinyl Pyrollidone (k 30) | 3.00 |
| 4. | Isopropyl Alcohol (IPA) | QS |
| 5. | Ramipril | 5.00 |
| 6. | Hydroxy Propyl Methyl Cellulose 5 cps (HPMC) | 0.20 |
| 7. | Pregelatinised Starch (Starch 1500) | 49.80 |
| 8. | Hydrochlorothiazide (HCTZ) | 12.50 |
| 9. | Lactose anhydrous (DCL 21) | 113.50 |
| 10. | Polyplasdone XL 10 | 4.00 |
| 11. | Pregelatinised Starch (Starch 1500) | 50.00 |
| | Granules Weight | 365.00 |
| | Aspirin tablet | |
| | Core | |
| 1. | Aspirin | 100.00 |
| 2. | Pregelatinised Starch (Starch 1500 ®) | 4.35 |
| 3. | Microcrystalline Cellulose (Avicel PH 200 ®) | 8.18 |
| 4. | Sodium Lauryl Sulphate | 0.15 |
| 5. | Colloidal Silicondioxide | 3.00 |
| 6. | Stearic Acid | 2.32 |
| | Coat I | |
| 1. | Ethyl cellulose 7 cps | 2.00 |
| 2. | Hydroxy Propyl Methyl Cellulose (5 CPS) (HPMC) | 0.50 |
| 3. | Isopropyl Alcohol (IPA) | QS |
| 4. | Methylene Dichloride (MDC) | QS |
| | Coat II | |
| 1. | Hydroxy Propyl Methyl Cellulose Phthalate | 11.89 |
| 2. | Isopropyl Alcohol | QS |
| 3. | Methylene Dichloride | QS |
| | Coat III | |
| 1. | Insta moist shield ® (HPMC based) | 2.61 |
| 2. | Isopropyl Alcohol | QS |
| 3. | Methylene Dichloride | QS |
| | Tablet Weight | 136.00 |
| | Final Lubrication | |
| 1. | Sodium Stearyl Fumarate | 4.00 |
| 2. | Colloidal Silicondioxide | 3.00 |

Simvastatin and Aspirin tablets along with Atenolol, Ramipril and HCTZ blend were filed in hard gelatin capsules.

Example 7 Multi Component Pharmaceutical Composition Having Improved Stability

The present example illustrates certain aspects of the invention in greater detail and is not intended to limit the scope of the invention.

| S. No. | Ingredients | Quantity (mg/cap.) |
|---|---|---|
| | Aspirin tablet | |
| | Core | |
| 1. | Aspirin | 100.00 |
| 2. | Pregelatinised Starch (Starch 1500 ®) | 4.35 |
| 3. | Microcrystalline Cellulose (Avicel PH 200 ®) | 3.20 |
| 4. | Sodium Lauryl Sulphate | 0.15 |
| 5. | Colloidal Silicondioxide | 3.0 |
| 6. | Stearic Acid | 2.30 |
| | Core tablet weight (mg) | 113.00 |
| | Coat I | |
| 1. | Ethyl cellulose 7 cps | 0.45 |
| 2. | Hydroxy Propyl Methyl Cellulose (5 CPS) (HPMC) | 1.90 |
| 3. | Isopropyl Alcohol (IPA) | QS |
| 4. | Methylene Dichloride (MDC) | QS |
| 5. | Propylene glycol | 0.15 |
| | Tablet weight | 115.50 |
| | Coat II | |
| 1. | Hydroxy Propyl Methyl Cellulose Phthalate | 11.90 |
| 2. | Isopropyl Alcohol | QS |
| 3. | Methylene Dichloride | QS |
| | Tablet weight (mg) | 127.40 |
| | Coat III | |
| 1. | Insta moist shield ® (HPMC based) | 2.60 |
| 2. | Isopropyl Alcohol | QS |
| 3. | Methylene Dichloride | QS |
| | Tablet Weight | 130.00 |
| | Simvastatin Granules | |
| 1. | Simvastatin | 21.0 |
| 2. | Colloidal Silicondioxide | 0.50 |
| 3. | Lactose anhydrous (DCL21) | 98.42 |
| 4. | Pregelatinised Starch (Starch 1500) | 10.0 |
| 5. | Butylated Hydroxy Anisole | 0.08 |
| 6. | Isopropyl Alcohol | QS |
| | Granules Weight | 130.00 |
| | Atenolol Granules | |
| 1. | Atenolol | 52.50 |
| 2. | Microcrystalline Cellulose (Avicel PH 101) | 74.50 |
| 3. | Poly Vinyl Pyrollidone (k 30) | 3.00 |
| 4. | Isopropyl Alcohol (IPA) | QS |
| | Granules Weight | 130.00 |
| | Ramipril Granules | |
| 1. | Ramipril | 5.25 |
| 2. | Hydroxy Propyl Methyl Cellulose 5 cps (HPMC) | 0.20 |
| 3. | Isopropyl Alcohol | QS |
| 4. | Methylene Dichloride (MDC) | QS |
| 5. | Pregelatinised Starch (Starch 1500) | 49.55 |
| | Granules Weight | 55.00 |

-continued

| S. No. | Ingredients | Quantity (mg/cap.) |
|---|---|---|
| | HCTZ Blend | |
| 1. | Hydrochlorothiazide (HCTZ) | 13.75 |
| 2. | Lactose anhydrous (DCL 21) | 59.25 |
| 3. | Pregelatinised Starch (Starch 1500) | 50.00 |
| | Granules Weight | 123.00 |
| | Final Lubrication | |
| 1. | Sodium Stearyl Fumarate | 4.00 |
| 2. | Colloidal Silicondioxide | 3.00 |

Manufacturing Process

Aspirin Tablet:
Tablet Compression
1. Aspirin was sifted through 20# and Starch 1500, Avicel PH-200, SLS & Aerosil through sieve #40 using mechanical sifter.
2. The above blend was mixed in double cone blender for 15 minutes and lubricated with with sodium stearyl Fumarate and passed through sieve #40 for 5 mins.
3. The blend was compressed using 6 mm punch.

Coat I
1. Ethyl Cellulose and HPMC, was dispersed in mixture of IPA/MDC under continuous stirring.
2. The tablets were coated with the above seal coating material to achieve the required weight gain.

Coat II
1. HPMC was dispersed in mixture of IPA/MDC under continuous stirring.
2. The tablets were coated with the above coating material to achieve the required weight gain.

Coat III
1. Instamoist shield was dispersed in mixture of IPA/MDC under continuous stirring.
2. The tablets were coated with the above coating material to achieve the required weight gain.

Simvastatin Granules:
1. All the ingredients were Sifted through 20#, mix for 10 minutes in RMG and granulated with IPA-BHA solution.
2. The wet mass was dried and milled through 0.5 mm Multimill.

Ramipril Granules:
1. Ramipril was Sifted though 20# and granulated it using HPMC dispersed in IPA-MDC.
2. The wet mass was dried below 40° C. and sifts through 40#.
3. The Starch 1500 was mixed to the above mass.

Atenolol Granules:
1. All the excipients were passed through 30#, dry mix for 10 minutes in RMG and granulated with PVP K 30 in IPA.
2. The wet mass was dried and milled through 0.5 mm Multimill.

HCTZ Blend:
1. All the ingredients were Sifted through 20#, mixed for 10 minutes Final Blending:
1. Atenolol blend and Ramipril blend was mixed for 15 minutes at 20 rpm.
2. To the above mass, Simvastatin blend, pre-sifted HCTZ, Lactose Anhydrous and Starch 1500 were added and mixed for 30 minutes at 20 rpm.

Lubrication:
The above mass was lubricated with Colloidal silicon dioxide and Sodium steryl fumarate for 5 minutes.

The aspirin tablet and blend of simvastatin, Atenolol, Ramipril and hydrochlorothiazide were filled in hard gelatin capsule.

The pharmaceutical composition incorporating above tablet was found to be stable at accelerated conditions, which is equivalent to a shelf life of more then 24 months.

Example 8

The following example of multi-constituent pharmaceutical composition is found to provide actives which are stable in nature.

| S. No. | INGREDIENTS | Mg/Capsule |
|---|---|---|
| | Part A: Dry Blend | |
| 1 | Simvastatin | 20.51 |
| 2 | Ramipril | 5.11 |
| 3 | Atenolol | 50.75 |
| 4 | Hydrochlorothiazide | 12.81 |
| 5 | Pregelatinised Starch | 202.82 |
| 6 | Lactose (Direct Compression Grade) | 100.00 |
| 7 | Sodium Stearyl Fumarate | 4.00 |
| 8 | Sodium Lauryl Sulphate | 4.00 |
| | Part B: Aspirin Enteric Coated Tablets | |
| | I) Aspirin Core Tablet | |
| 1 | Aspirin Granules | 100.25 |
| 2 | Sodium Starch Glycolate | 13.00 |
| 3 | Microcrystalline Cellulose (Avicel pH 200) | 20.00 |
| 4 | Colloidal Silicon Dioxide | 2.00 |
| 5 | Sodium Stearyl Fumarate | 2.00 |
| | II) Seal Coating of Aspirin Core Tablet | |
| 1 | Hypromellose -5 cps | 3.15 |
| 2 | Poly Ethylene Glycol 6000 | 0.15 |
| 3 | Isopropyl Alcohol | q.s |
| 4 | Calcium Carbonate | 0.06 |
| 5 | Talc | 0.31 |
| 6 | *Isopropyl Alcohol 35% | q.s |
| 7 | *Methylene Chloride 65% | q.s |
| | III) Enteric Coating of Aspirin Seal Coated Tablet | |
| 1 | Eudragit L30 D-55 | 10.03 |
| 2 | Triethyl Citrate | 0.35 |
| 3 | Talc | 0.90 |
| 4 | *Water | q.s |

*doesn't remain in final formulation

Manufacturing Process:

Part A: Dry Blend:
1. Simvastatin, Ramipril, Atenolol, Hydrochlorothiazide, Pregelatinised Starch, Lactose, Sodium Stearyl Fumarate and Sodium lauryl sulphate were sifted and mixed thoroughly.

Part B: Aspirin Enteric Coated Tablets
1. Aspirin granules, Sodium starch glycolate, microcrystalline cellulose, Colloidal silicon dioxide and sodium Stearyl Fumarate were used to manufacture core tablets of Aspirin. The tablets were manufactured by direct compression.
2. The Aspirin core tablets were seal coated.
3. The Seal coated aspirin tablets were enteric coated.

The blend from Part A and enteric coated tablet of aspirin from part B were filled in hard gelatin capsule.

Example 9

The following examples of Multi Component Composition is in tablet dosage form.

Example 9A

| Sr. No. | Ingredients | Quantity (mg/tab) |
|---|---|---|
| | Layer-I Part-I: Simvastatin Granules | |
| 1. | Simvastatin | 20.00 |
| 2. | Colloidal Silicondioxide | 0.50 |
| 3. | Lactose anhydrous (DCL21) | 98.42 |
| 4. | Pregelatinised Starch (Starch 1500) | 8.70 |
| 5. | Butylated Hydroxy Anisole | 0.08 |
| 6. | Isopropyl Alcohol | QS |
| 7. | Magnesium Stearate | 1.30 |
| | Layer-II Part-II: HCTZ Blend | |
| 1. | Hydrochlorothiazide (HCTZ) | 12.50 |
| 2. | Lactose anhydrous (DCL 21) | 59.25 |
| 3. | Pregelatinised Starch (Starch 1500) | 48.50 |
| 4. | Magnesium Stearate | 1.50 |
| | Layer-III: Part-III: Atenolol Granules | |
| 1. | Atenolol | 50.00 |
| 2. | Microcrystalline cellulose (Avicel pH 200) | 35.50 |
| 3. | Sodium stearyl glycolate | 10.00 |
| 4. | Silicon dioxide (Aerosil) | 1.50 |
| 5. | Magnesium Stearate | 5.00 |
| 6. | Isopropyl alcohol | qs |
| | Part-IV: Ramipril Granules | |
| 1. | Ramipril | 5.00 |
| 2. | Hydroxy Propyl Methyl Cellulose 5 cps (HPMC) | 0.20 |
| 3. | Isopropyl Alcohol | QS |
| 4. | Methylene Bichloride (MDC) | QS |
| 5. | Pregelatinised Starch (Starch 1500) | 49.55 |
| | Coating | |
| 6. | Coating Material | 10.00 |

Manufacturing Process:

Layer I (Part I): Simvastatin Granules:
1. All the ingredients (S.No: 1-4) were sifted through 20#, mix for 10 minutes in RMG and granulated with IPA-BHA solution.
2. The wet mass was dried and milled through 0.5 mm Multimill.
3. The dried granules were lubricated with Magnesium stearate.

Layer II (Part II): HCTZ Blend:
1. All the ingredients were Sifted through 20#, mixed for 10 minutes Layer III (Part III): Atenolol Granules
1. All the excipients (S.No: 1-4) were passed through 30#, dry mix for 10 minutes in RMG and granulated with PVP K 30 in IPA.
2. The wet mass was dried and milled through 0.5 mm Multimill.
3. The dried granules were lubricated with Magnesium stearate.

Layer III (Part IV): Ramipril Granules:
1. Ramipril was Sifted though 20# and granulated it using HPMC dispersed in IPA-MDC.
2. The wet mass was dried below 40° C. and sifts through 40#.
3. The Starch 1500 was mixed to the above mass.

To prepare the layered tablets, layer I, layer II and layer III mixtures were sequentially compressed into trilayered tablets, which finally were film coated.

Example 9B

| Sr. No. | Ingredients | Quantity (mg/tab) |
|---|---|---|
| | Layer-I | |
| | Part-I: Simvastatin Granules from example 4A equivalent to Simvastatin | 20.00 |
| | Layer-II | |
| | Part-II: HCTZ blend from example 4D equivalent to HCTZ | 12.50 |
| | Part-III: Atenolol Granules example 4B equivalent to Atenolol | 50.00 |
| | Part-IV: Ramipril Granules example 4C equivalent to Ramipril | 5.00 |
| | Talc | 3.00 |
| | Magnesium Stearate | 6.00 |

The granules according to example 9B are prepared by the process disclosed in example 4A-D. To prepare the layered tablets, layer I and layer II mixtures were lubricated with Talc and Magnesium Stearate separately followed by sequentially compressing into bilayered tablets, which finally were film coated.

Example 9C

| Sr. No. | Ingredients | Quantity (mg/tab) |
|---|---|---|
| | Single Layer | |
| | Part-I: Simvastatin Granules from example 4A equivalent to Simvastatin | 20.00 |
| | Part-II: HCTZ blend from example 4D equivalent to HCTZ | 12.50 |
| | Part-III: Atenolol Granules example 4B equivalent to Atenolol | 50.00 |
| | Part-IV: Ramipril Granules example 4C equivalent to Ramipril | 5.00 |
| | Talc | 2.50 |
| | Magnesium Stearate | 5.00 |

The granules according to example 9C are prepared by the process disclosed in example 4A-D. To prepare the tablets Part-I to IV mixtures were mixed and lubricated with Talc and Magnesium Stearate followed by compression into tablets, which finally were film coated.

I. Formulations with adverse event profile is not worse than a single ingredient included in the composition.

Formulation of example 7 has been evaluated in a clinical trial for safety. It was compared with various components in a double blind controlled study to demonstrates the above.

a. The change in SGPT by two fold, S. Potassium above 5.5 and increase in serum creatinine by 50% was to be marginally higher in a group taking aspirin 100 mg (n=172) compared group taking MCP (n=334) daily for three months as per example.

b. All reported Adverse events documented in a three month trial duration were 163 in a group of 205 taking aspirin, 161 in a group of 205 taking thiazide, 166 in a group of 205 taking simvastatin alone compared to 313 in a group of 412 taking multi-component pill.

c. There was no preponderance of adverse events attributable to any of the component in multi-component pill group compared to other groups containing one or two of the ingredients.

d. Serious adverse leading to discontinuation
   a. Dizziness and hypotension was found to be higher (3.3% vs 2.6%) in Thiazide group (n=199) compared to MCP (n=392)
   b. Cough was found be in 1.4% in a group receiving Ramipril compared to 0.2% in a group receiving MCP.
   c. Gastritis/dyspepsia was found in 1.4% taking Aspirin (n=197) compared to 0.5% taking MCP (n=392)

II. In a cross over randomized two period study pharmacokinetic parameters were evaluated following administration of single MCP as a test and a market preparation containing single ingredient pill as a reference product.

a) Formulations with more than one antihypertensive drugs which when consumed provides serum level of antihypertensive drugs which are no different then achieved by consumption of a single ingredient.

The following tables summaries the pharmacokinetic parameter. They are also provided by FIGS. 1 to 5.

TABLE 1

Statistical Summary of Ln-transformed Pharmacokinetic Parameters of Ramipril (n = 36)

| Parameter | Test Geo LSM | Ref. Geo LSM | Ratio (T/R) * 100 | 90% CI (%) | Intra CV (%) | Power |
|---|---|---|---|---|---|---|
| Ln $C_{max}$ (ng/mL) | 17.049 | 14.386 | 118.51 | 99.65-140.96 | 44.88 | 0.6849 |
| Ln $AUC_{0-t}$ (hr × ng/mL) | 13.656 | 12.417 | 109.98 | 99.31-121.79 | 25.61 | 0.9737 |
| Ln $AUC_{o-\infty}$ (hr × ng/mL) | 14.425 | 13.223 | 109.09 | 98.91-120.30 | 24.54 | 0.9812 |

TABLE 2

Statistical Summary of Ln-transformed Pharmacokinetic Parameters of Ramiprilat (n = 36)

| Parameter | Test Geo LSM | Ref. Geo LSM | Ratio (T/R) * 100 | 90% CI (%) | Intra CV (%) | Power |
|---|---|---|---|---|---|---|
| Ln $C_{max}$ (ng/mL) | 14.102 | 12.001 | 117.50 | 103.87-132.93 | 31.19 | 0.9101 |
| Ln $AUC_{0-t}$ (hr × ng/mL) | 260.040 | 246.919 | 105.31 | 99.94-110.97 | 12.99 | 1.0000 |
| Ln $AUC_{o-\infty}$ (hr × ng/mL) | 355.324 | 335.438 | 105.93 | 97.97-114.54 | 19.48 | 0.9982 |

TABLE 3

Statistical Summary of Ln-transformed Pharmacokinetic Parameters of Atenolol (n = 35)

| Parameter | Test Geo LSM | Ref. Geo LSM | Ratio (T/R) * 100 | 90% CI (%) | Intra CV (%) | Power |
|---|---|---|---|---|---|---|
| Ln $C_{max}$ (ng/mL) | 357.508 | 374.496 | 95.46 | 85.00-107.21 | 27.36 | 0.9362 |
| Ln $AUC_{0-t}$ (hr × ng/mL) | 2894.499 | 2982.038 | 97.0687 | 81-107.30 | 23.52 | 0.9770 |
| Ln $AUC_{o-\infty}$ (hr × ng/mL) | 3034.591 | 3132.195 | 96.88 | 88.21-106.42 | 21.99 | 0.9869 |

TABLE 4

Statistical Summary of Ln-transformed Pharmacokinetic Parameters of Hydrochlorthiazide (n = 36)

| Parameter | Test Geo LSM | Ref. Geo LSM | Ratio (T/R) * 100 | 90% CI (%) | Intra CV (%) | Power |
|---|---|---|---|---|---|---|
| Ln $C_{max}$ (ng/mL) | 93.437 | 92.388 | 101.14 | 90.92-112.50 | 25.91 | 0.9637 |
| Ln $AUC_{0-t}$ (hr × ng/mL) | 579.174 | 621.884 | 93.13 | 86.90-99.81 | 16.70 | 0.9997 |
| Ln $AUC_{o-\infty}$ (hr × ng/mL) | 619.693 | 668.583 | 92.69 | 86.81-98.97 | 15.79 | 0.9999 | b) Formulations with anti-platelet agent along with other ingredients in such a way that its consumption do not result in blood levels identical to achieved with consumption of anti-platelet agent alone.

TABLE 5

Statistical Summary of Ln-transformed Pharmacokinetic Parameters of Salicylic Acid (n = 36)

| Parameter | Test Geo LSM | Ref. Geo LSM | Ratio (T/R) * 100 | 90% CI (%) | Intra CV (%) | Power |
|---|---|---|---|---|---|---|
| Ln $C_{max}$ (ng/mL) | 4826.592 | 4851.948 | 99.48 | 89.83-110.16 | 24.19 | 0.9736 |
| Ln $AUC_{0-t}$ (hr × ng/mL) | 25373.013 | 21586.127 | 117.54 | 105.77-130.62 | 25.04 | 0.9660 |
| Ln $AUC_{0-\infty}$ (hr × ng/mL) | 26327.867 | 22346.380 | 117.82 | 106.06-130.87 | 24.94 | 0.9669 | c) Consumption of MCP does not result in blood levels of active metabolite of lipid lowering agent (simvastatic acid) lower than the one achieved with consumption of a lipid lowering agent alone (simvastatin).

III. Formulation of example has been evaluated in a clinical trail for efficacy along with other formulation containing one or more actives.

1. A pharmaceutical composition comprising of multiple antihypertensive drugs in such a way that effect on sitting systolic and diastolic B.P. is more than each ingredient.

a) Reduction in sitting diastolic and sitting systolic blood pressure was measured in a cohort of population who received multi-component pill or a pill containing one antihypertensive drugs.

Mean change in sitting diastolic blood pressure was 5.0 mm of Hg and of Hg with multi-component pill compared to 1.2 mm of Hg when hydrochlorothiazide (n=199) was consumed. Mean change in sitting systolic blood pressure was 6.9 mm of Hg with multi-component pill (n=392) compared to 2.2 mm mm of Hg when hydrochlorothiazide is used. Thus the effect with Multi-component pill was better than hydrochlorthiazide.

b) Reduction in sitting diastolic and sitting systolic blood pressure was measured in a cohort of population who received multi-component pill (n=392) or a pill containing two antihypertensive drugs (n=207,205,209).

Mean change in sitting blood pressure was 5.0 mm of Hg and of Hg with multi-component pill compared to 3.6 mm when two antihypertensive drugs were consumed. Mean change in sitting systolic blood pressure was 6.9 mm of Hg with multi-component pill compared to 4.7 mm mm of Hg. Thus the effect with multi-component pill was better than two drugs.

Surprisingly the effect on blood pressure is found to be lower than predicted (5.0 vs 11.0 for diastolic B.P.)

2. A pharmaceutical composition comprising of multiple antihypertensive drugs (three or more) in such a way that effect on sitting systolic and diastolic B.P. is identical to three antihypertensive drugs.

Reduction in sitting diastolic and sitting systolic blood pressure was measured in a cohort of population who received multi-component pill (n=392) or a pill containing three antihypertensive drugs (n=196).

Mean change in sitting diastolic blood pressure was 5.0 mm of Hg when multi-component pill or pill containing three antihypertensive drugs was consumed. Mean change in sitting systolic blood pressure was 6.9 mm of Hg when multi-component pill or pill containing three antihypertensive drugs was consumed.

3. A pharmaceutical composition containing B-blocker as one of active ingredient where in reduction in heart rate is non inferior to those seen with other beta-blocker containing compositions.

a) In a randomized controlled study the effect of atenolol containing formulation on sitting heart rate was evaluated in various formulations containing atenolol with other drugs. Hydrochlorothiazide with atenolol and multi-component pill containing simvastatin, atenolol, hydrochlorothiazide, ramipril and aspirin were evaluated. All received a pill a day. The mean difference in drop in heart rate was found to be identical in both the groups. (7.86 and 7.41) The no. of subjects in multi-component pill was 411 and that in other group was. 207.

b) In a randomized controlled study normal healthy volunteers (16 in each group) were given either atenolol or multi-component pill. The heart rate was measured for 24 hrs. The decrease in heart rate was identical in both groups. Peak decrease in heart rate was seen at 4.5 hrs. It was 5.38 for atenolol group and 5.43 for multi-component pill.

4. A pharmaceutical composition containing lipid modifying drugs in such a way effect on lipid is non inferior to that observed when lipid modifying drug is taken alone.

Effect of lipid modifying drug in a multi-component composition is not inferior to the effect seen following administration of lipid lowering drug alone.

In a randomized double blind controlled study 198 subjects received simvastatin 20 mg daily for 3 months while 406 subjects received simvastatin 20 mg as one of the ingredient of multi-component pharmaceutical composition. The multi-component pharmaceutical composition included

| Ramipril | 5 mg |
|---|---|
| Hydrochlorothiazide | 12.5 mg |
| Atenolol | 50 mg |
| Aspirin | 100 mg beside Simvastatin 20 mg |

The change in lipid profile as compared to baseline is provided in a table below.

| | Total Cholesterol | LDL | Apo B |
|---|---|---|---|
| Simvastatin | 17.95% | 26.83% | 20.37% |
| Multi-component Pharmaceutical composition | 17.07% | 24.6% | 17.98% |

5. Effect has also been found in hypertensive as well as nonhypertensives. Compared to hypertensives the effect is significantly better in nonhypertnsive with multi-component pill compared to single ingredient.

|  | Drug | Hypertensive | Non hypertensive |
|---|---|---|---|
| Systolic B.P. | Thiazide | 3.0 | 1.8 |
|  | MCP | 8.4 | 6.1 |
| Diastolic B.P. | Thiazide | 2.5 | 0.5 |
|  | MCP | 5.9 | 4.5 |

6. Effect has also been found in diabetics as well as non-diabetics. Compared to diabetics the effect is significantly better in nondiabetics compared to single ingredient.

|  | Drug | Diabetics | Non diabetics |
|---|---|---|---|
| Systolic B.P. | Thiazide | 3.4 | 1.6 |
|  | MCP | 8.4 | 6.2 |
| Diastolic B.P. | Thiazide | 1.5 | 1.1 |
|  | MCP | 5.2 | 5.0 |

7. Urinary thromboxane levels were found to be identical in a group taking aspirin and MCP suggesting no lose of antiplatelet activity.

What is claimed is:

1. A stable solid oral pharmaceutical composition comprising
    1) granules of Atenolol devoid of organic acid,
    2) granules of Simvastatin devoid of organic acid,
    3) Ramipril, and
    4) Hydrochlorothiazide;
   wherein the Simvastatin and Atenolol have been granulated separately using alcoholic binder solution, without aqueous or hydroalcoholic binder solution.

2. The pharmaceutical composition according to claim 1 is a capsule.

3. The pharmaceutical composition according to claim 1, wherein Simvastatin is in the form of a tablet and is separated from other active ingredients within a capsule.

4. The pharmaceutical composition according to claim 1, wherein Ramipril and Atenolol are granulated before incorporating into a capsule.

5. The pharmaceutical composition as claimed in claim 1, further containing Aspirin and/or other platelet aggregating inhibitor as active ingredient.

6. The pharmaceutical composition according to claim 5, wherein Aspirin is enteric coated and separated from other active ingredients.

7. The pharmaceutical composition according to claim 1, wherein the amount of Simvastatin is about 5 mg to about 80 mg, the amount of Atenolol is about 6 mg to about 100 mg, the amount of Ramipril is about 1.25 mg to about 20 mg, and the amount of hydrochlorothiazide is about 6 mg to about 50 mg.

8. The pharmaceutical composition according to claim 1 is used for treating atherosclerosis.

9. The pharmaceutical composition according to claim 1 is used to treat the progression of atherosclerosis.

10. The pharmaceutical composition according to claim 1, wherein the said composition is devoid of drug-drug interaction.

11. A stable solid oral pharmaceutical composition comprising:
    granules of Atenolol devoid of organic acid,
    granules of Simvastatin devoid of organic acid,
    Ramipril,
    Hydrochlorothiazide, and
    a pharmaceutically acceptable excipient,
    wherein the Simvastatin and Atenolol have been granulated separately using alcoholic binder solution, without aqueous or hydroalcoholic binder solution; and
    said pharmaceutical composition is stable at accelerated conditions, which is equivalent to a shelf life of more than 24 months.

* * * * *